United States Patent
Guchelaar et al.

(10) Patent No.: US 8,073,630 B2
(45) Date of Patent: Dec. 6, 2011

(54) PHARACOGENETIC METHOD FOR PREDICTION OF THE EFFICACY OF METHOTREXATE MONOTHERAPY IN RECENT-ONSET ARTHRITIS

(75) Inventors: Hendrik Jan Guchelaar, AB Gouda (NL); Tom Willem Johannes Huizinga, ND Leiden (NL)

(73) Assignee: Exagen Diagnostics, Inc., Albuquerque, NM (US)

( * ) Notice: Subject to any disclaimer, the term of this patent is extended or adjusted under 35 U.S.C. 154(b) by 1033 days.

(21) Appl. No.: 11/846,406

(22) Filed: Aug. 28, 2007

(65) Prior Publication Data
US 2008/0288177 A1 Nov. 20, 2008

Related U.S. Application Data

(60) Provisional application No. 60/840,973, filed on Aug. 30, 2006.

(51) Int. Cl.
*G06F 7/00* (2006.01)
(52) U.S. Cl. .............. 702/19; 702/20; 703/11; 707/700; 436/501; 435/6.1; 435/7.1; 536/24.1
(58) Field of Classification Search ........................ None
See application file for complete search history.

(56) References Cited

U.S. PATENT DOCUMENTS

| 7,702,469 | B2 | 4/2010 | Huizinga et al. |
| 7,713,696 | B2 | 5/2010 | Guchelaar et al. |
| 2009/0029379 | A1 | 1/2009 | Guchelaar et al. |
| 2010/0240541 | A1 | 9/2010 | Guchelaar et al. |

FOREIGN PATENT DOCUMENTS
WO    WO 2005/022118 A2    3/2005

OTHER PUBLICATIONS

Wessels et all 2007 Arthritis and Rheumatism 56, 6, 1756-1775.*
Gervaisini 2009 Genes and metabolism, 10, 547-566.*
Chan et al., *Molecular action of methotrexate in inflammatory diseases*, Arthritis Research, vol. 4 No. 4, 266-273, (2002).
Krajinovic et al., *Role of Polymorphisms in MTHFR and MTHFD1 genes in the outcome of childhood acute lymphoblastic leukemia*, The Pharmacogenomics Journal, vol. 4, 66-72 (2004).
Kalsi et al., *Decreased cardiac activity of AMP deaminase in subjects with the AMPD1 mutation—A Potential Mechanism of Protection in heart failure*, Cardiovascular Research, vol. 59, 678-684 (2003).
Dervieux et al., *Polyglutamation of Methotrexate with common Polymorphisms in Reduced Folate Carrier, Aminoimidazole Carboxamide Ribonucleotide Transformylase, and Thymidylate Synthase are associated with methotrexate effects in Rheumatoid Arthritis*, Arthritis & Rheumatism, vol. 50 No. 9, 2766-2774 (2004).
Sumi et al., *Genetic basis of inosine triphosphate pyrophosphohydrolase deficiency*, Hum Genet, vol. 111, 360-367 (2002).
Wessels et al., *Efficacy and Toxicity of Methotrexate in Early Rheumatoid Arthritis are associated with single-nucleotide polymorphisms in genes coding for folate pathway enzymes*, Arthritis & Rheumatism, vol. 54 No. 4, 1087-1095 (2006).
Raganathan et al., *Will pharmacogenetics allow better prediction of methorexate toxicity and efficacy in patients with rheumatoid arthritis?*, Ann Rheum. Dis., vol. 62, 4-9 (2002).
Johnston et al., *The Anti-inflammatory action of methotrexate is not mediated by lymphocyte apoptosis, but by the suppression of activation and adhesion molecules*, Clinical Immunology, vol. 114, 154-163 (2005).
Raganathan et al., *Single nucleotide polymorphism profiling across the methotrexate pathway in normal subjects and patients with rheumatoid arthritis*, Pharmacogenomics, vol. 5 No. 5, 559-569, (2004).
Hoekstra et al., *Factors associated with toxicity, final dose, and efficacy of methotrexate in patients with rheumatoid arthritis*, Ann Rheum. Dis. vol. 62, 423-426 (2003).
International Search Report and Written Opinion based on International Application PCT/NL2007/050420, 16 pages, mailed Dec. 3, 2007.
Green et al., "Persistence of mild, early inflammatory arthritis: The importance of disease duration, rheumatoid factor, and the shared epitope," Arthritis and Rheumatism 42(10):2184-2188 (1999).
Wessels et al., "Relationship between genetic variants in the adenosine pathway and outcome of methotrexate treatment in patients with recent-onset rheumatoid arthritis," Arthritis and Rheumatism 54(9):2830-2839 (2006).
Wessels et al., "A clinical pharmacogenetic model to predict the efficacy of methotrexate monotherapy in recent-onset rheumatoid arthritis," Arthritis and Rheumatism 56(6):1765-1775 (2007).

* cited by examiner

*Primary Examiner* — Mary Zeman
(74) *Attorney, Agent, or Firm* — McDonnell Boehnen Hulbert & Berghoff LLP

(57) ABSTRACT

Pharmacogenetic methods for determining a predicting responsiveness to antifolate therapy for subjects that present with recent-onset undifferentiated arthritis. The methods are based on the determination of a set of clinical parameter values and determining a predicted responsiveness to antifolate therapy by correlating the parameter values with pre-defined responsiveness values associated with ranges of parameter values. Parameters values that are decisive for responsiveness to antifolate therapy may include polymorphisms in the methylenetetrahydrofolate dehydrogenase (MTHFD1) gene as well as in three genes involved in the adenosine release pathway, the presence or absence of Rheumatoid factors, gender, pre- or postmenopausal status and/or smoking status.

33 Claims, 3 Drawing Sheets

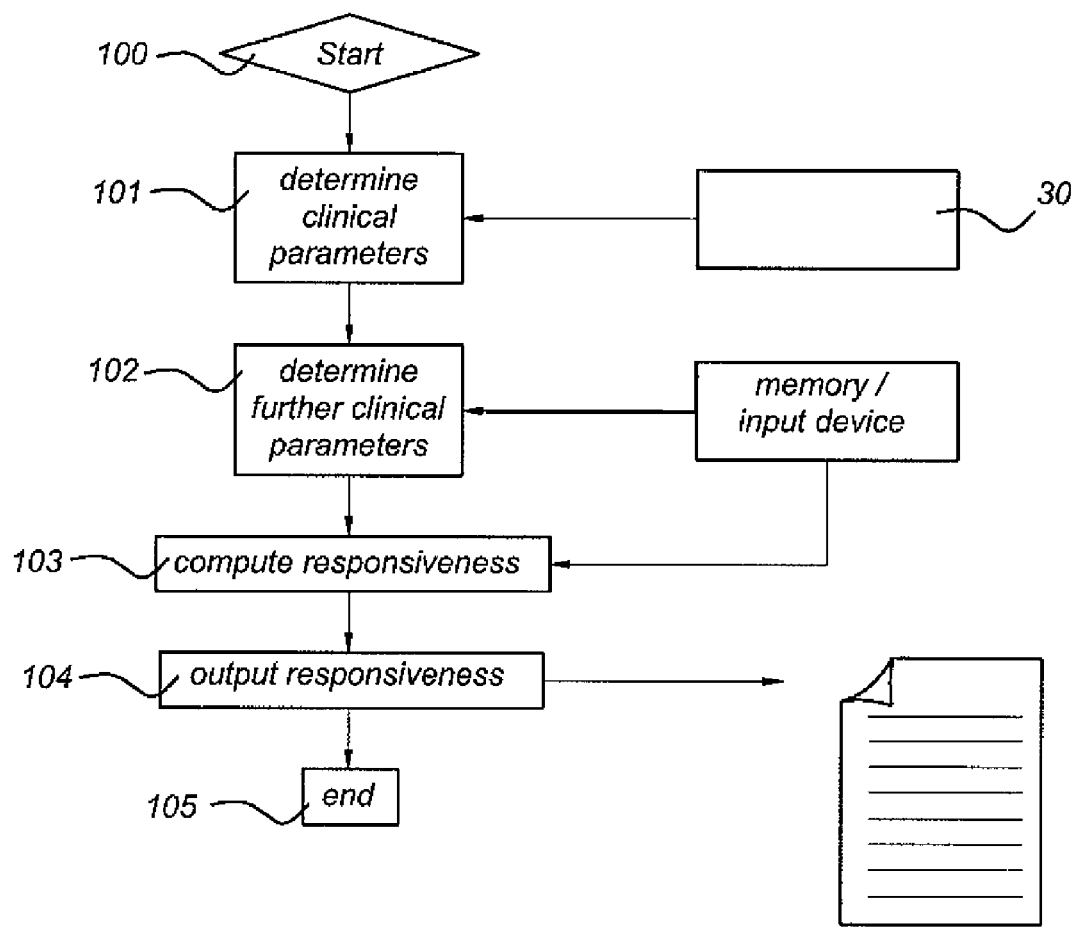

PHARACOGENETIC METHOD FOR PREDICTION OF THE EFFICACY OF METHOTREXATE MONOTHERAPY IN RECENT-ONSET ARTHRITIS

RELATED APPLICATIONS

This application claims priority under 35 U.S.C. §119(e) to U.S. Provisional Application No. 60/840,973, filed Aug. 30, 2006, the entire contents of which are incorporated herein by reference

SEQUENCE LISTING

The present application is being filed along with a Sequence Listing in electronic format. The Sequence Listing is provided as a file entitled PROPR_17A_SeqListing.txt, created Aug. 28, 2007, which is 17.2 Kb in size. The information in the electronic format of the Sequence Listing is incorporated herein by reference in its entirety.

FIELD OF THE INVENTION

The current invention relates to the field of medicine, in particular the fields of methotrexate monotherapy in recent-onset arthritis and the pharmacogenetic diagnostics and prognostics thereof.

BACKGROUND OF THE INVENTION

Individualized treatment decision-making is one of the most important challenges of medicine. To this end, a number of studies have recently appeared that associate clinical variables or gene-expression profile with disease outcome, thereby providing help for clinicians in treatment decisions in several diseases (e.g. Hodgkin disease, lymphoma).

Disease activity in rheumatoid arthritis (RA) leads to progressive joint and cartilage destruction. (1) Patients with active RA generally experience declining functionality and disability within two years of disease onset. (2) RA treatment is, since the last decennium, characterized by earlier and more intensive treatment with disease-modifying antirheumatic drugs (DMARDs), as this treatment strategy prevents joint damage and functional disability. Recent clinical studies demonstrate that early therapeutic intervention with combination strategies, with or without anti-tumor necrosis factor agents (anti-TNF agents) are superior to monotherapy with DMARDs and considerably improves RA prognosis. (3-5)

Although combination strategies are more efficacious, such intensive approach is probably not necessary for all newly diagnosed RA patients. (6; 7) In addition, combination treatment with anti-TNF agents or corticosteroids possibly introduces patients to other risks, such as serious infections or osteoporosis. (8; 9) As a result, it is important to determine whether patients have a high probability of response to monotherapy to preclude or prescribe combination treatment.

Methotrexate (MTX) is the most widely used DMARD in clinical practice, although the factors determining MTX efficacy are largely unknown. The influences of demographic, clinical immunological and genetic factors on the state of disease in RA patients have been previously studied (10-18). Polymorphisms in genes encoding methylene tetrahydrofolate reductase (MTHFR), adenosine monophosphate deaminase (AMPD1), aminoimidazole carboxamide ribonucleotide transformylase (ATIC) and inosine triphosphate pyrophosphatase (ITPA) demonstrate an association with MTX response. (19-21) Non-genetic factors such as low disease activity at baseline, male sex, non-steroidal anti-inflammatory drug (NSAID) use and lower creatinine clearance are also related to MTX efficacy (22). However, these associations, alone or in combination, were not transformed into clinical decision tools to guide MTX treatment in patients.

Therefore, there is still a need to explore additional polymorphisms in genes that are associated with MTX response and a need for a clinical pharmacogenetic model that reliably predicts the efficacy of MTX monotherapy in patients with recent-onset arthritis.

SUMMARY OF THE INVENTION

In a first aspect, the present invention relates to methods for determining a predicted clinical responsiveness to antifolate therapy in a subject afflicted with, or at risk of developing, arthritis, such as rheumatoid arthritis (RA). In one embodiment, the methods described herein are applied to individuals that present with a recent-onset arthritis. In other embodiments, the methods described herein are applied to individuals with recent-onset undifferentiated arthritis or recent-onset rheumatoid arthritis. Undifferentiated arthritis (UA) is herein defined as arthritis for which with the available classification criteria no diagnosis can be made, e.g. using the American College of Rheumatology (ACR) 1987 classification criteria for RA (see e.g. Arnette et al., 1988, Arthritis Rheum. 31: 315-324). RA is herein defined as arthritis for which with the available classification criteria the diagnosis can be made, e.g. using these American College of Rheumatology (ACR) 1987 classification criteria for rheumatoid arthritis. An individual with recent-onset arthritis is herein defined as an individual with complaints dating from less than one year, (e.g., less than 6 months). An individual with recent-onset RA is herein defined as an individual with complaints dating from less than two years (e.g., less than one year). The methods described herein may also be applied to individuals that present with persistent RA, preferably to individuals wherein primary antifolate therapy and/or anti-TNF therapy has failed.

One embodiment provides a method for determining a predicted responsiveness to methotrexate (MTX) responsiveness in a mammal afflicted with, or at risk of developing, arthritis (e.g., RA) by determining one or more polymorphisms in one or more of the following genes: methylenetetrahydrofolate dehydrogenase (MTHFD1), adenosine monophosphate deaminase (AMPD1), aminoimidazole carboxamide ribonucleotide transformylase (ATIC), and inosine triphosphate pyrophosphatase (ITPA), wherein the presence of the polymorphism is indicative of clinical responsiveness to the antifolate therapy. The subject may be any mammal, including a human, ape, dog horse, cow, pig, rabbit and the like. In one embodiment, the method of the invention is performed in vitro on a sample obtained from a subject to be tested. The in vitro method may be performed on nucleic acid present in a sample from the subject, which may be any sample containing nucleic acids such as blood, serum, plasma, saliva, tissue, or a buccal swab. Nucleic acids which can be analyzed using the present methods include genomic DNA, genomic RNA, mRNA and cDNA.

BRIEF DESCRIPTION OF THE DRAWINGS

FIG. 3 schematically depicts a flow diagram of a procedure that may be executed by the computer of FIG. 2 according to an embodiment of the invention.

DETAILED DESCRIPTION OF THE PREFERRED EMBODIMENT

Figure 1:
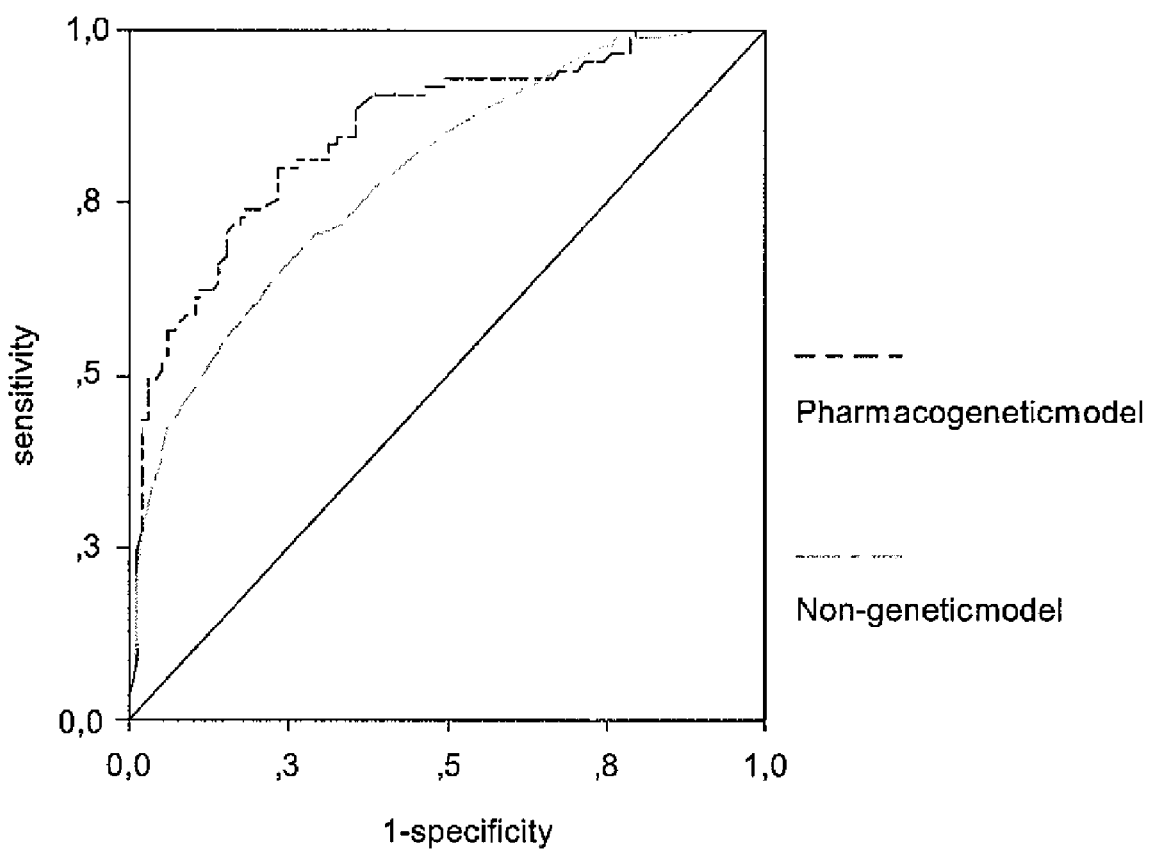
FIG. 1 shows a Receiver Operating Curve for predicting methotrexate response, including clinical and pharmacogenetic factors. Incorporated factors in the pharmacogenetic model are gender, Disease Activity Score (DAS) at baseline, rheumatoid factor (RF) status, smoking status, and genotypes for ATIC, AMPD1, ITPA and MTHFD1. Factors in the non-genetic model are gender, DAS at baseline, RF status, and smoking status.

As used herein, the term "antifolate" means a molecule that acts as a folate antagonist against one or more folate-dependent enzymes (e.g., thymidylate synthase and dihydrofolate reductase) and which may also be structurally similar to folate. These compounds result in reduction of de novo purine and pyrimidine synthesis. One antifolate, methotrexate, is also used for treatment of arthritis and rheumatoid arthritis. Although the examples described herein relate to methotrexate, the present methods are also suitable for predicting efficacy and toxicity of other antifolates, including aminopterin, trimetrexate, lometrexol, pemetrexed, 5-fluorouracil and leucovorin, as well as methotrexate analogs. As used herein, the term "methotrexate analog" means a molecule having structural and functional similarity to methotrexate. Methotrexate analogs are functionally characterized, in part, by their inhibitory activity against dihydrofolate reductase. These analogs include, but are not limited to, dichloromethotrexate, 7-methyl substituted methotrexate, 3',5'-difluoromethotrexate, and 7,8-dihydro-8-methyl-methotrexate. It will be understood that polyglutamate derivatives of the above antifolates and methotrexate analogs, such as e.g. MTX-polyglutamate, are also included in the term "antifolate".

As used herein, "polymorphism" refers to the occurrence of two or more genetically determined alternative sequences or alleles in a population. A "polymorphic site" refers to the locus at which divergence occurs. Preferred polymorphic sites have at least two alleles, each occurring at a frequency of greater than 1%. In other embodiments, each of the at least two alleles occurs at a frequency of greater than 10% or 20% of a selected population. A polymorphic locus may be as small as one base pair (single nucleotide polymorphism, or SNP). Polymorphic markers include restriction fragment length polymorphisms, variable number of tandem repeats (VNTRs), hypervariable regions, minisatellites, dinucleotide repeats, trinucleotide repeats, tetranucleotide repeats, simple sequence repeats, insertion elements such as Alu, deletions and differences in gene copy number. The first identified allele is arbitrarily designated as the reference allele and other alleles are designated as alternative or "variant alleles." The alleles occurring most frequently in a selected population may be referred to as the "wild-type" allele. Diploid organisms may be homozygous or heterozygous for the variant alleles. The variant allele may or may not produce an observable physical or biochemical characteristic ("phenotype") in an individual carrying the variant allele. For example, a variant allele may alter the enzymatic activity of a protein encoded by a gene of interest.

One type of polymorphism is a "single nucleotide polymorphism" or "SNP." A SNP occurs at a polymorphic site occupied by a single nucleotide, which is the site of variation between allelic sequences. The site is usually preceded by and followed by highly conserved sequences of the allele (e.g., sequences that vary in less than 1/100 or 1/1000 members of the populations). A SNP usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

In a first embodiment of the invention, the method comprises detecting the presence of a polymorphism in the methylenetetrahydrofolate dehydrogenase (MTHFD1) gene, wherein the presence of the polymorphism is indicative of clinical responsiveness to the antifolate therapy. Methylenetetrahydrofolate dehydrogenase (EC 1.5.1.15) is encoded by the MTHFD1 gene (accession number for the human gene: NM_005956). In one embodiment, the polymorphism in the MTHFD1 gene is a polymorphism that results in an amino acid change with respect to the amino acid sequence of SEQ ID NO: 1. One polymorphism in the MTHFD1 gene for detection in the methods of the invention is the single nucleotide polymorphism 1958G>A (rs17850560). In one embodiment, a genotype that is indicative of clinical responsiveness to the antifolate therapy is a MTHFD1 G-allele carrier. The genotype "MTHFD1 1958 G-allele carrier" is understood to mean a genotype that is homozygous or heterozygous for the MTHFD1 1958 G-allele.

In another embodiment, polymorphisms in one or more genes involved in the adenosine release pathway are determined, wherein the presence of the polymorphism is indicative of clinical responsiveness to the antifolate therapy. Genes involved in the adenosine release pathway for detection of polymorphism that are indicative of clinical responsiveness to the antifolate therapy include one or more of the following genes: adenosine monophosphate deaminase (AMPD1), aminoimidazole carboxamide ribonucleotide transformylase (ATIC), and inosine triphosphate pyrophosphatase (ITPA).

Adenosine monophosphate deaminase (EC 3.5.4.6) is encoded by the AMPD1 gene (accession number for the human gene: NM_000036). In one embodiment, the polymorphism in the AMPD1 gene is a polymorphism that results in an amino acid change with respect to the amino acid sequence of SEQ ID NO: 2. One particular polymorphism in the AMPD1 gene for detection in the methods of the invention is the single nucleotide polymorphism 34C>T (rs17602729). In another embodiment, an AMPD1 genotype that is indicative of clinical responsiveness to the antifolate therapy is an AMPD1 34 T-allele carrier.

Aminoimidazole carboxamide ribonucleotide transformylase (ATIC) (EC 6.3.2.6) is encoded by the ATIC gene (accession number for the human gene: NM_004044). In one embodiment, the polymorphism in the ATIC gene is a polymorphism that results in an amino acid change with respect to the amino acid sequence of SEQ ID NO: 3. One particular polymorphism in the ATIC gene for detection in the methods described herein is the single nucleotide polymorphism 347 C>G (rs2372536). One particular ATIC genotype that is indicative of clinical responsiveness to the antifolate therapy is the ATIC 347 CC genotype. The "ATIC 347 CC genotype" is understood to mean the genotype that is homozygous for the ATIC 347 C allele.

Inosine triphosphate pyrophosphatase (EC 3.6.1.19) is encoded by the ITPA gene (accession number for the human gene: NM_033453). In one embodiment, the polymorphism in the ITPA gene is a polymorphism that results in an amino acid change with respect to the amino acid sequence of SEQ ID NO: 4. One particular polymorphism in the ITPA gene for detection in the methods of the invention is the single nucleotide polymorphism 94 C>A (rs1127354). In another embodiment, an ITPA genotype that is indicative of clinical responsiveness to the antifolate therapy is the ITPA 94 CC genotype.

Without wishing to be bound by any specific theory, adenosine is thought to mediate the antirheumatic effects of MTX via adenosine receptor signaling. Binding of this compound to specific receptors enhances the anti-inflammatory properties of methotrexate. For example, the AMPD1 34C>T mutation generates an AMP-deaminase enzyme with lower activity. AMPD1 catalyzes the conversion of adenosine-monophosphate (AMP) to inosine-monophosphate (IMP). Alternatively, AMP is converted to adenosine. Thus, deficiency of AMPD1 could enhance adenosine release. Other mutations and/or polymorphisms having an effect on AMPD1 activity in vivo may have similar or even more pronounced effects on MTX. In addition, both ITPA and ATIC activity could lead to formation of adenosine. ITPA polymorphisms have been shown to lead to ITPA deficiency, which results in decreased IMP levels as ITPA catalyzes the conversion of inosine triphosphate (ITP) to IMP. Since this enzyme influences the cellular IMP level, it may influence its balance with AMP and adenosine. Furthermore, methotrexate inhibits ATIC which leads to cellular accumulation of AICAR, a nucleoside precursor which inhibits adenosine deaminase (ADA), resulting in reduced conversion of adenosine to inosine.

In one embodiment, the method comprises detecting the presence of a polymorphism in each of the genes encoding methylenetetrahydrofolate dehydrogenase (MTHFD1) gene, adenosine monophosphate deaminase (AMPD1), aminoimidazole carboxamide ribonucleotide transformylase (ATIC), and inosine triphosphate pyrophosphatase (ITPA) wherein the presence of a polymorphism in at least one of these four genes is indicative of clinical responsiveness to the antifolate therapy, whereby, the polymorphisms for each of the four genes may be as defined hereinabove.

It will be appreciated that the present methods are not limited to these polymorphisms. Other polymorphisms (e.g., SNPs) in any of the MTHFD1, AMPD1, ATIC, and ITPA genes may also be used. In one embodiment, the polymorphism has a frequency in a population of 1%, 5%, 10%, 20% or more, and results in an amino acid change resulting in a functional change for the gene product or enzyme, such as an amino acid change with respect to the amino acid sequences of SEQ ID NO: 1-4, respectively. These functional changes may include e.g. biochemical activity, stability/half-life and interaction with other proteins or compounds. Polymorphisms in non-coding regions of the MTHFD1, AMPD1, ATIC, and ITPA genes, leading to altered rates of transcription, translation, regulation or splicing, may also be used. Also silent polymorphisms in coding regions, or in the promoter region of a gene, which have no effect on the translated protein, may however affect translation rates or efficiency and thereby affect the enzyme's activity level. These polymorphisms may thus also be used in the diagnostic methods described herein.

The present methods may be performed using any known biological or biochemical method in which genetic polymorphisms, such as SNPs, can be detected or visualized. Such methods include, but are not limited to, DNA sequencing, allele specific PCR, PCR amplification followed by an allele/mutant specific restriction digestion, oligonucleotide ligation assays, primer hybridization and primer extension assays, optionally combined with or facilitated by microarray analysis. Alternative methods for determining allelic variants and gene polymorphisms are readily available to the skilled person in the art of molecular diagnostics.

Another embodiment is oligonucleotides capable of hybridizing to sequences in or flanking genes (e.g., polymorphic regions) involved in adenosine metabolism, and the use of these oligonucleotides for performing these methods. Primers may be designed to amplify (e.g., by PCR) at least a fragment of a gene encoding an adenosine metabolism-associated enzyme. A polymorphism may be present within the amplified sequence and may be detected by, for example, a restriction enzyme digestion or hybridization assay. The polymorphism may also be located at the 3' end of the primer or oligonucleotide, thus providing means for an allele or polymorphism specific amplification, primer extension or oligonucleotide ligation reaction, optionally with a labeled nucleotide or oligonucleotide. The label may be an enzyme (e.g., alkaline phosphatase, horseradish peroxidase), radiolabel ($^{32}P$, $^{33}P$, $^{3}H$, $^{125}I$, $^{35}S$ etc.), a fluorescent label (Cy3, Cy5, GFP, EGFP, FITC, TRITC and the like) or a hapten/ligand (e.g., digoxigenin, biotin, HA, etc.). In one embodiment, the detection is carried out using oligonucleotides physically linked to a solid support, and may be performed in a microarray format.

Another embodiment is a kit comprising one or more oligonucleotides capable of hybridizing to, or adjacent to, any of the polymorphic sites in any of the MTHFD1, AMPD1, ATIC, and ITPA genes as defined hereinabove. The oligonucleotide(s) may be provided in solid form, in solution or attached on a solid carrier such as a DNA microarray. In addition, the kit may provide detection means, containers comprising solutions and/or enzymes and a manual with instructions for use.

In another embodiment of the methods described herein for determining a predicted clinical responsiveness to antifolate therapy in a subject afflicted with, or at risk of developing, arthritis, the method further comprises the step of: a) determining the clinical responsiveness to the antifolate therapy by correlating the presence of a polymorphism as defined hereinabove with a predefined responsiveness value associated with each particular polymorphism. In one embodiment, a responsiveness score is calculated as the sum of the responsiveness values for each polymorphism.

In one embodiment of the methods of the invention, the method further comprises the step of: b) determining a set of clinical parameter values comprising at least one of:
  i) the gender of the subject and optionally the pre- or postmenopausal status of a female subject;
  ii) DAS at baseline, wherein DAS is disease activity score as defined by the European League Against Rheumatism;
  iii) the presence or absence of Rheumatoid factor; and,
  iv) smoking status; and
c) determining the predicted clinical responsiveness to the antifolate therapy by correlating the values determined in steps a) and b) with a predefined responsiveness value associated with each particular polymorphism and parameter value.

In the methods described herein, the DAS28 may be used, which is the disease activity score as defined by the European League Against Rheumatism based on a swollen joint count of 28 joints. In another embodiment, the DAS44 is used, which is a more extensive disease activity score that is based on a swollen joint count of 44 joints.

In one embodiment, a responsiveness score is calculated as the sum of the responsiveness values for each polymorphism and for each parameter value. The individual responsiveness values for the polymorphisms and clinical parameters may be defined as between 50% and 150%, between 75% and 125%, between 80% and 120% or between 90% and 110% of the values in a)-i):

a) 0 for male gender; 1 for female gender;
b) 0 for DAS at baseline$\leq$3.8;
   2.8 for DAS at baseline>3.8, but $\leq$5.1;
   3.4 for DAS at baseline>5.1;
c) 0 for Rheumatoid factor negative and non-smoker;
   0.8 for Rheumatoid factor negative and smoker;
   0.75 for Rheumatoid factor positive and non-smoker;
   2.2 for Rheumatoid factor positive and smoker;
d) 0.98 for MTHFD1 1958 AA genotype;
e) 1.2 for AMPD1 34 CC genotype;
f) 1.7 for ITPA A-allele carrier;
h) 1.1 for ATIC 347 G-allele carrier; and,
i) 0 for other genotypes;
and whereby the maximum responsiveness score is between 11.0 and 12.0, for example 11.5.

In another embodiment, the individual responsiveness values for the polymorphisms and clinical parameters are defined as between 75% and 125%, between 80% and 120%, between 90% and 110% of the values in a)-i):
a) 0 for male gender; 1 for female gender;
b) 0 for DAS at baseline$\leq$3.8;
   3 for DAS at baseline>3.8, but $\leq$5.1;
   3.5 for DAS at baseline>5.1;
c) 0 for Rheumatoid factor negative and non-smoker;
   1 for Rheumatoid factor negative and smoker;
   1 for Rheumatoid factor positive and non-smoker;
   2 for Rheumatoid factor positive and smoker;
d) 1 for MTHFD1 1958 AA genotype;
e) 1 for AMPD1 34 CC genotype;
f) 2 for ITPA A-allele carrier;
h) 1 for ATIC 347 G-allele carrier; and,
i) 0 for other genotypes.
and whereby the maximum responsiveness score is 11.5.

A subset of the clinical parameters a) to i) may also be used, in which case it will be understood that the maximum responsiveness score is calculated as the sum of the responsiveness values for each polymorphism and for each parameter value in the subset.

In the methods described herein, a responsiveness score of a subject of 6 or more may indicate that the subject is not responsive to antifolate therapy. Subjects with a responsiveness score of 6 or more are not eligible for antifolate monotherapy and are instead given a combination therapy. A responsiveness score of a subject less than 6 indicates that the subject is eligible for antifolate monotherapy. However, for subjects with a responsiveness score that is less than 6, a distinction may be made between a responsiveness score of more than 3.5 but less than 6 and a responsiveness score of 3.5 or less. A subject with a responsiveness score of more than 3.5 but less than 6 indicates that the subject has an intermediate responsiveness to antifolate therapy. Subjects with an intermediate responsiveness to antifolate therapy may be started on antifolate therapy, for example with a weekly dose of about 15 mg MTX or equivalent thereto. After some period of time (e.g. about 3 months), the DAS of the subjects may be established and: a) if a decrease in DAS of more than 1.2 is measured, antifolate monotherapy is continued but the dosage is increased to about 25 mg weekly; or b) if a decrease in DAS of 1.2 or less is measured, antifolate monotherapy is discontinued and combination therapy is started. Subjects with a responsiveness score of 3.5 or less may be started on antifolate monotherapy (e.g., about 15 mg MTX weekly or equivalent thereto), and if necessary (DAS>2.4) after some period of time (e.g. about 3 months) the dosage may be increased to about 25 mg weekly.

Further embodiments of the invention will now be described with reference to the accompanying figures, wherein like numerals refer to like elements throughout.

Figure 2:
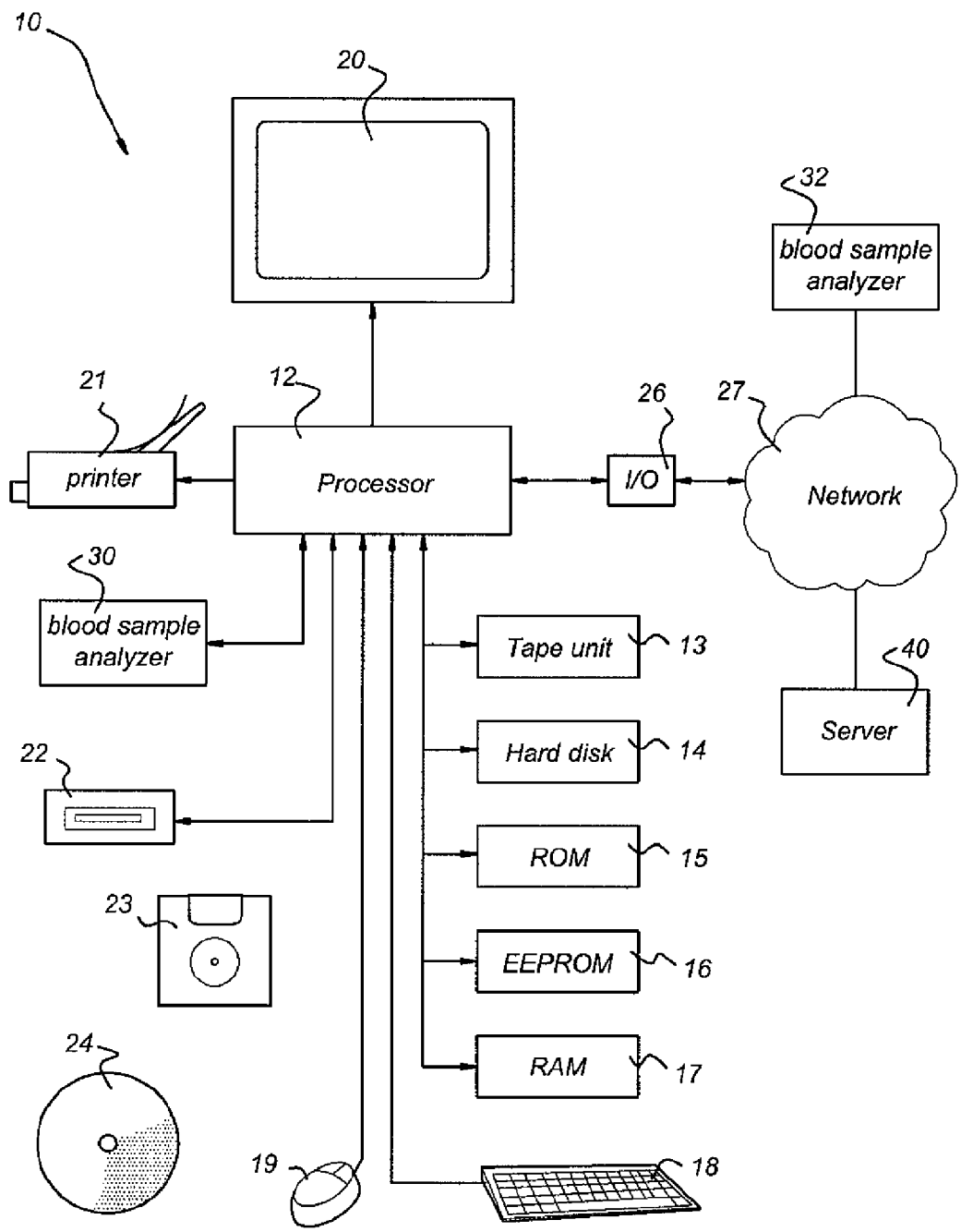
FIG. 2 shows a schematic example of an embodiment of a computer that may be used in one or more of the embodiments described.

FIG. 2 shows a schematic example of an embodiment of a computer 10 that may be used in one or more of the embodiments described herein. As illustrated in exemplary FIG. 2, the computer 10 comprises a processor 12 for performing mathematical operations. The processor 12 is connected to memory units that may store instructions and data, such as a tape unit 13, hard disk 14, a Read Only Memory (ROM) 15, Electrically Erasable Programmable Read Only Memory (EEPROM) 16 and a Random Access Memory (RAM) 17. The processor 12 is also connected to one or more input devices, such as a keyboard 18 and a mouse 19, one or more output devices, such as a display 20 and a printer 21, and one or more reading units 22 to read, for example, floppy disks 23 or CD ROMs 24. In one embodiment, the computer system 10 comprises program lines readable and executable by the processor 12.

The computer 10 shown in FIG. 2 may also comprise an input output device (I/O) 26 arranged to communicate with other computer systems (not shown) via a communication network 27. In the exemplary embodiment of FIG. 2, sample analyzer 32 is in data communication with the network 27. In the embodiment of FIG. 2, a local sample analyzer 30 is located proximate the computer 10 and a remote sample analyzer 32 is positioned remote the computer 10 and may be in communication with the computer 10 via the network 27. In certain embodiments, any number of sample analyzers 30, 32 may be in communication with the computer 10. For example, in one embodiment, the system does not include a local sample analyzer 30, but comprises multiple remote sample analyzers 32.

In the embodiment shown in FIG. 2, a server 40 is also in data communication with the network 27. In certain embodiments, the server 40 stores data received from the sample analyzer 30,32 and provides this data to the computer 10. In other embodiments, the server 40 and/or the sample analyzer 30,32 are configured to perform operations on data determined by the sample analyzer 30,32 in order to determine the predicted responsiveness to antifolate therapy of an subject, such as by using the systems and methods described below. The following description refers to the computer 10 as the device that performs calculations in order to determine the predicted responsiveness of a subject to antifolate therapy. However, any other computing device, such as the sample analyzer 30,32 or the server 40 may also be configured to perform these operations and determine the predicted responsiveness of an subject to antifolate therapy.

In one embodiment, the computer 10 accesses information and software executing on the server 40 via a graphical user interface, such as a web browser, that is displayed on the display device 20. In this embodiment, the computer 10 provides an interface for viewing, such as by a physician, data from the sample analyzer 30 that is stored on the server 40. In one embodiment, the user interface that is displayed on the display device 20 may include data received from the sample analyzer 30 via the network 27.

In one embodiment, the computer 10 comprises more and/or other memory units, input devices and read devices than are illustrated in FIG. 2. Moreover, one or more of them may be physically located remote from the processor 12, if required. The exemplary processor 12 is shown as one box, but may comprise several processing units functioning in parallel or controlled by one main processor unit that may be located remote from one another, as is known to persons skilled in the art.

It is observed that, although all connections in FIG. 2 are shown as physical connections, one or more of these connections can be made wireless. They are only intended to show that "connected" units are arranged to communicate with one another in some way.

The computer 10 is shown as a computer system, but can be any signal processing system with analog and/or digital and/or software technology arranged to perform the functions discussed herein.

The detailed description as given above for the computer 10 may refer to several kind of devices, such as personal computers, servers, laptops, personal digital assistance (PDA), palmtops. All of these devices are different kinds of computer systems.

The memory units 13, 14, 15, 16, 17 may comprise program lines readable and executable by the processor 12. The programming lines may be such that they provide the computer 10 with the functionality to perform one or more of the methods described below.

As noted above, the computer 10 may be connected to a sample analyzer 30, 32 by a communication link. The sample analyzer 30, 32 may be arranged to receive a blood sample, or other biological sample, from an individual and perform measurements on this blood sample. The sample analyzer 30, 32 may, for example, be arranged to determine a set of clinical parameter values from the blood sample including:
  i) the gender of the subject and, optionally, the pre- or postmenopausal status of a female subject;
  ii) DAS at baseline, wherein DAS is disease activity score as defined by the European League Against Rheumatism; the presence or absence of Rheumatoid factor;
  iii) smoking status;
  iv) the presence or absence of Rheumatoid factor; and/or
  v) one or more the polymorphisms/genotypes defined hereinabove.

In the embodiment shown in FIG. 2, the computer 10 is arranged for receiving data-signals relating to measurements of a blood sample from the sample analyzer 30, 32 so as to determine clinical parameter values for a set of clinical parameters, such as the parameters i)-v) noted above. In one embodiment, the connection between the computer 10 and the sample analyzer 30 comprises a wired and/or wireless two-way communication link, such as via a direct wired or wireless connection 32 or via the network 27. Alternatively, in case clinical parameter values are determined by different sample analyzers, the computer 10 may also comprise multiple connections, each to one of the different sample analyzers 30.

The computer 10 may be arranged to read the at least one clinical parameter as determined by the sample analyzer 30, 32, and store the at least one clinical parameter in the memory units 13, 14, 15, 16, 17.

The computer 10 may also determine the at least one clinical parameter by reading the at least one clinical parameter from memory 13, 14, 15, 16, 17, or from input devices, such as keyboard 18 and mouse 19, or from one or more reading units 22 to read for instance floppy disks 23 or CD ROMs 24.

In other embodiments, fewer or additional further clinical parameters may be received by the computer 10 and used to determine the predicted responsiveness to antifolate therapy. In one embodiment, for example, the further clinical parameter values are entered into the computer 10 using one or more input devices, such as a keyboard and/or a mouse, in response to information displayed in a graphical user interface that is displayed on the display device 20. For example, a graphical user interface may be configured to prompt a user to enter each of a plurality of clinical parameter values. In one embodiment, each of the entered clinical parameter values is used to determine the predicted responsiveness to antifolate therapy. In other embodiments, selected clinical parameter values are used to determine the predicted responsiveness to antifolate therapy. In one embodiment, a confidence level in the predicted responsiveness increases as the number of clinical parameter values that are entered into the graphical user interface, and are processed by the computer 10, increases. Thus, while the predicted responsiveness may be determined based on as few as two clinical parameter values, the confidence level of the predicted responsiveness may increase as additional clinical parameter values are received and considered in determining the predicted responsiveness.

In one embodiment, the computer 10 may be arranged to read these further parameter values from memory 13, 14, 15, 16, 17, from input devices, such as keyboard 18 and mouse 19, or from one or more reading units 22 to read, for example, floppy disks 23 or CD ROMs 24.

As noted above, the computer 10 may be arranged to determine the predicted responsiveness of an subject to antifolate therapy by correlating at least two of the clinical parameter values with a predefined responsiveness value associated with each particular parameter value. The responsiveness score may be outputted by the computer 10 using one or more output devices, such as display 20 and printer 21. Also, computer 10 may be arranged for transmission of the predicted responsiveness value over the network 27 to another computer system (not shown).

In one embodiment, the predicted responsiveness is transmitted to a remote computing system and displayed to a user via a graphical user interface. In another embodiment, the predicted responsiveness is transmitted via e-mail to the individual, a physician, and/or another computing system. In yet another embodiment, the predicted responsiveness may be transmitted via facsimile or printed and delivered to the individual and/or physician. In certain embodiments, the responsiveness values associated with each of the clinical parameter values and the total responsiveness value or score for the individual are also transmitted from the computer 10 to another computing device. In one embodiment, the predicated responsiveness is stored on the server 40 and is accessible to users with proper authorization to view the predicted responsiveness, such as the subject and the subject's healthcare providers.

FIG. 3 schematically depicts a flow diagram of a procedure as may be executed by computer 10, or other computing device, according to an embodiment described herein. Depending on the embodiment, certain of the actions described below may be removed, others may be added, and the sequence of actions may be altered.

In a first action 100, the computer 10 starts executing the procedure. This action may be triggered, for example, by input from a user into a graphical user interface displayed on the display device 20.

In a next action 101, the computer 10 determines at least one clinical parameter using sample analyzer 30, 32. This action may comprise the steps of 101*a*) the processor 12 requesting the sample analyzer 30, 32 to output data-signals relating to the measured values of a blood sample to the processor 12; 101*b*) the processor 12 receiving the data-signals, and 101*c*) the processor 12 (optionally) storing the data-signals relating to the measured values in memory 13, 14, 15, 16, 17. In one embodiment, the data-signals that are received from the sample analyzer 30, 32, comprise parameter values associated with each of one or more clinical parameters, such as, for example, a parameter value indicating a polymorphism or genotype as defined hereinabove and a parameter value indicating the presence or absence of Rheumatoid factor in the sample (e.g., blood sample). In one embodiment, action 101*a*) may also comprise that the processor 12 requests the sample analyzer 30, 32 to perform certain measurements on the sample (e.g., blood sample) relating to determining a set of clinical parameter values, such as clinical parameters values for clinical parameters i)-v) discussed above before transmitting the data-signals.

In a next action 102, the processor 12 determines at least one of the further clinical parameter values using one or more input devices as described above, or alternatively, from associated data already stored in memory 13, 14, 15, 16, 17. As noted above, the further clinical parameter values may be entered into a computing device, such as computer 10, via a graphical user interface. In one embodiment, the further clinical parameter values are entered into the computer 10 by a caregiver in response to comments from the individual. In another embodiment, a user interface is accessible to the individual via a computer in communication with the network, so that the individual may enter the further clinical parameter values for use in this method.

In a further action 103, the computer 10 determines the predicted responsiveness of a subject to antifolate therapy by correlating each of at least two of the clinical parameter values and further clinical parameter values determined in action 101 and 102 above with predefined responsiveness values that are associated with each particular parameter value. These responsiveness values may then be combined in order to determine a total responsiveness value or score for the individual. Finally, the total responsiveness value or score may be associated with the predicted responsiveness of a subject to antifolate therapy. In one embodiment, ranges of values for each of the clinical parameter values are associated with particular responsiveness values. In another embodiment, responsiveness values for particular clinical parameters are determined according to formulas specific to each clinical parameter. In one embodiment, the total responsiveness value or responsiveness score is the sum of each of the responsiveness values that have been associated with the clinical parameter values. In other embodiments, the total responsiveness value may be calculated using only a portion of the responsiveness values.

In one embodiment, ranges of total responsiveness values are each associated with the responsiveness of the subject to antifolate therapy. The number of ranges of total responsiveness values and the granularity of the predicted responsiveness associated with the ranges may vary depending on the application. For example, in one embodiment only two ranges of total responsiveness values are used, where total responsiveness values that are within a first range are associated with predicted responsiveness indicating that an individual is likely to respond to antifolate therapy, and total responsiveness values that are within a second range are associated with predicted responsiveness indicating that the individual is not likely to respond to antifolate therapy. In another embodiment, total responsiveness values are associated with one of three predicted responsivenesses, such as low, intermediate, and high responsiveness to antifolate therapy. In other embodiments, total responsiveness values are each associated with one of a plurality, such as 5, 10, 15, or 20, for example, of different predicted responsiveness scores. In one embodiment, the predicted responsiveness scores are expressed as a percentage chance that the individual will respond to antifolate therapy. In one embodiment, the predicted responsiveness is determined based on a formula in which the total responsiveness value is a factor. In this embodiment, ranges of total responsiveness values may not be necessary as each total responsiveness value may result in a different predicted responsiveness.

In one embodiment, the predefined responsiveness values associated with parameter values, or ranges of parameter values, may be stored in memory 13, 14, 15, 16, 17 and retrieved from memory 13, 14, 15, 16, 17 by the processor 12, or may be received using input devices as described above.

In a next action 104, the computer 10 outputs the computed predicted responsiveness of a subject to antifolate therapy using one or more output devices, such as display 20 and printer 21, or by transmission of the computed predicted responsiveness to another computer system (not shown), such as via email or storage of the predicted responsiveness on a server that is accessible to other users. Also, the computer 10 may store the computed predicted responsiveness, and/or the responsiveness values and total responsiveness values, in memory 13, 14, 15, 16, 17 or on the server 40.

In action 105, the execution of procedure ends. If needed, the procedure may be resumed at action 101 to execute once more.

According to a further embodiment, the sample analyzer 30, 32 and/or the server 40 comprises a computer, having the components such as those described above with reference to computer 10, that is configured to perform the procedure described in FIG. 3. Thus, in one embodiment the sample analyzer 30, 32 and/or server 40 are capable of computing the antifolate responsiveness score of a subject by correlating at least two of the clinical parameter values determined above with a predefined responsiveness value associated with each particular parameter value.

One embodiment relates to a method for determining a predicted responsiveness of a subject to antifolate therapy, the method comprising: a) receiving characteristics of a subject, the characteristics comprising at least two of: a polymorphism as defined in hereinabove, and an indicator of a presence or absence of Rheumatoid factor in a blood sample from the subject; b) assigning a responsiveness value to each of the characteristics; and, c) determining a predicted responsiveness of the subject to antifolate therapy, the predicted responsiveness being determined based at least partly on the determined responsiveness values. In the method, at least some of the characteristics may be received from a blood sample analyzer. In one embodiment, the received characteristics include indicators of least one of: i) the gender of the subject and optionally the pre- or postmenopausal status of a female subject; ii) DAS at baseline, wherein DAS is disease activity score as defined by the European League Against Rheumatism; and, iii) smoking status. In another embodiment, at least some of the characteristics are entered into a user interface that communicates the characteristics via one or more networks. The method may further comprise transmitting the predicted responsiveness via email, and may further comprise transmitting the predicted responsiveness to a server that is accessible to authorized users. The authorized users may comprise at least one of the subject and a healthcare provider for the subject. The assigning may comprise accessing data in a computer memory associating responsiveness values with characteristics. In the method, the determined predicted responsiveness is expressed as a percentage chance that the subject responds to antifolate therapy.

Another embodiment relates to a system for determining a predicted responsiveness of an subject to antifolate therapy, comprising: a) means for receiving characteristics of a subject, the characteristics comprising at least two polymorphisms described herein, and an indicator of a presence or absence of Rheumatoid factor in a blood sample from the subject; b) means for assigning a responsiveness value to each of the characteristics; and, c) means for determining a predicted responsiveness of the subject to antifolate therapy, the predicted responsiveness being determined based at least partly on the determined responsiveness values.

Again another preferred embodiment relates to a system for determining a predicted responsiveness of an subject to antifolate therapy, the system comprising: a) a blood sample analyzer configured to analyze a blood sample provided by the individual and determine at least two polymorphisms as described herein, and an indicator of a presence or absence of Rheumatoid factor in a blood sample from the subject; and, b) a computing device configured to assign a responsiveness value to each of the indicators determined by the blood sample analyzer, wherein the computing device accesses data stored in a memory associating ranges of values for each of the indicators with respective responsiveness values, the computing device further configured to determine a predicted responsiveness of the subject to antifolate therapy based at least partly on the assigned responsiveness values. The system, the blood sample analyzer may be located remote from or proximate to the computing device and the indicators may be transmitted to the computing device via a network communication link. The computing device may be further configured to transmit one or more electronic messages indicating the determined predicted responsiveness. The computing device may receive the indicators via a web interface in data communication with the computing device. The computing device may be further configured to assign a risk value to indicators indicating at least one of: i) the gender of the subject and optionally the pre- or postmenopausal status of a female subject; ii) DAS at baseline, wherein DAS is disease activity score as defined by the European League Against Rheumatism; and iii) smoking status.

The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described. In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

EXAMPLES

Example 1

Methods
RA Patient Population

The 205 patients enrolled in this study comprised a subcohort of the 508 patients who participated in the BeSt study. (5) The BeSt study is a randomized, multicenter, single-blinded, clinical study comparing the clinical efficacy of four different treatment strategies in recent onset RA including sequential monotherapy (n=126 starting with MTX), step up to combination therapy of MTX with sulfasalazine (SSZ, n=121 starting with MTX), initial combination therapy with MTX, SSZ and a high tapered dose of prednisolone (n=133), or initial biologic therapy with infliximab plus MTX (n=128). Inclusion criteria for patients in the study comprise the American College of Rheumatology (ACR) 1987 criteria for RA (23), an age $\geq$18 years, and a disease duration of <2 years. Patients were also required to have active RA, defined as $\geq$6 swollen joints (out of 66) and $\geq$6 tender joints (out of 68) and either an erythrocyte sedimentation rate (ESR) $\geq$28 mm/hour or a score of $\geq$20 mm on 100 mm visual analogue scale (VAS) for patient's assessment of global health (0=best, 100=worst). Individuals were ineligible for the BeSt study if they were previously treated with DMARDs other than antimalarial agents or were receiving concomitant treatment with an experimental drug. The local ethics committee at each participating hospital approved the study protocol. All patients gave informed consent before enrolment into the study.

Study Design and Treatment

Patients allocated initial monotherapy with MTX with available DNA samples (n=205) were included in the current analysis. The primary goal of therapy in the BeSt study groups was clinical response as defined by the European League Against Rheumatism (EULAR) Disease Activity Score (DAS) of $\leq$2.4. (24; 25) The DAS is a validated composite outcome measure consisting of the Ritchie articular index (RAI), the number of swollen joints (SJC, out of 44: DAS44), general well-being as indicated by the patient on a visual analogue scale (VAS) and the erythrocyte sedimentation rate (ESR). A research nurse who was blinded to the allocated treatment group assessed the DAS every 3 months.

All patients included in this analysis began on a regime of oral MTX 7.5 mg weekly, increasing to 15 mg weekly after 4 weeks, in combination with folic acid (1 mg daily). In the event of insufficient clinical response (DAS>2.4) at the 3-month follow-up visit, the MTX dosage was increased stepwise to 25 mg weekly. In case of adverse drug events, MTX was continued at the lowest tolerated dose. In case of intolerance, MTX could also be given parenterally. The patient was treated according to the next treatment step if MTX was not tolerated at all. Concomitant treatment with nonsteroidal anti-inflammatory drugs (NSAIDs) and intra-articular injections with corticosteroids were allowed for all treatment groups. For the current analysis, clinical data for the first 6 months of follow up were used to represent MTX treatment only.

MTX Response Evaluation

"Responders" were defined as patients with a DAS of $\leq$2.4 (good clinical response) based on EULAR response criteria and using MTX at 6 months (24; 25). "Non-responders" were defined as patients with a DAS of >2.4 at the 6-month follow up visit and using MTX. Of the 205 patients, 19 patients were missing for efficacy analyses; 2 patients moved, 1 patient refused to take MTX after short usage without having adverse drug events (ADEs), 5 patients did not have their DAS assessed, 1 patient started on sulfasalazine before evaluation, 10 patients had discontinued MTX permanently after experiencing ADEs. Consequently, 186 remained eligible for MTX efficacy evaluation at 6 months. Patients experiencing ADEs, but still treated with MTX at 6 months, were included in the analysis.

Selection of Demographic, Clinical and Immunological Factors

Baseline variables possibly influencing the patient's disease state and MTX response were selected on the basis of literature. (10-18; 21; 22; 26; 27). The following factors were identified: gender; rheumatoid factor status; age; duration of joint complaints; alcohol consumption; smoking; body mass index; menopausal status; hormone supplementation; VAS for physician's assessment of disease activity, for pain, for patients assessment of disease activity, for patient's assessment of global health, for morning stiffness; Health assessment questionnaire (HAQ); ESR; C-reactive protein (CRP); DAS; SJC; RAI; kidney function (defined as creatinine clearance); anti-cyclic citrullinated peptide status (CCP); NSAID use and the existence of co-morbidity based on drug use (other than RA disease-related drugs). The CCP assay was not performed for all patients at the time of inclusion in the BeSt study. As CCP status is unlikely to change with treatment (27), the CCP status after beginning treatment was also used.

Selection of Single Nucleotide Polymorphisms

Seventeen single nucleotide polymorphisms (SNPs) in 13 candidate genes related to MTX mechanism of action, purine and pyrimidine synthesis (28-30), were selected taking the following criteria into consideration (31; 32): validated SNP, SNP—preferably—causes non-synonymous amino acid change, indications for clinical relevance from previous publications and a preferred minimal genotype frequency of approximately 10%. (19-21; 33-46)

All DNA was isolated from peripheral white blood cells by the standard manual salting-out method. Positive (Applied Biosystems Control DNA CEPH 347-02) and negative controls (water) were used for quality control. In addition, 5-10% of samples were genotyped in duplicate and no inconsistencies were observed.

Genotyping techniques, success rates and genotype frequencies of 10 out of the 17 SNPs in this population together with their association with MTX response were previously reported (19; 20). These SNPs were in genes encoding adenosine monophosphate deaminase (AMPD1), aminoimidazole carboxamide ribonucleotide transformylase (ATIC), inosine triphosphate pyrophosphatase (ITPA), methionine synthase (MTR), and methionine synthase reductase (MTRR), dihydrofolate reductase (DHFR), methylenetetrahydrofolate reductase (MTHFR) and the reduced folate carrier (RFC). The following SNPs were analyzed: MTHFR 677C>T (rs1801133), MTHFR 1298A>C (rs1801131), DHFR-473G>A (DNA alignment, rs1650697), DHFR 35289A>G (DNA alignment, rs1232027), RFC 80G>A (rs1051266), MTRR 66A>C (rs1801394), MTR 2756A>G (rs1805087), AMPD1 34C>T (rs17602729), ITPA 94C>A (rs1127354) and ATIC 347C>G (rs2372536).

Seven SNPs were de novo genotyped for this analysis in our population. These SNPs were in genes encoding methylenetetrahydrofolate dehydrogenase (MTHFD1), serine hydroxymethyltransferase (SHMT1), folylpolyglutamate synthase (FPGS), gamma-glutamyl hydrolase (GGH) and thymidylate synthetase (TYMS). The SNPs were MTHFD1 1958G>A (rs17850560), SHMT1 1420C>T (rs17829445), TYMS 28 bp-tandem repeat polymorphism in the promoter region, FPGS 114G>A (rs10760502), FPGS 1994A>G (DNA alignment, rs10106), GGH 452C>T (rs11545078) and GGH 16T>C (rs1800909).

Real-time polymerase chain reaction (PCR) using the Taqman technique were used in genotyping MTHFD1 and SHMT1. Both assays were performed according to protocols provided by the manufacturer (Taqman, Applied Biosystems, Foster City, Calif.). FPGS and GGH SNPs were genotyped using the Pyrosequencer method and protocols (Uppsala, Sweden). Double (2R2R) or triple (3R3R) 28 bp-tandem repeats in the promoter region of the TYMS gene were visualized on agarose gels directly after the PCR reaction.

Genotype distributions for MTHFD1 1958G>A were: 29% GG, 50% GA, 22% AA; for SHMT1: 1420C>T 54% CC, 42% CT, 4% TT; for FPCS: 114G>A 49% CG, 45% CA, 6% AA; for FPGS: 1994A>G 31% AA, 48% GA, 21% GG; for GGH: 452C>T 83% CC, 17% CT; for GGH: 16T>C 53% TT, 39% CT, 7% CC; and for TYMS 28-bp repeats: 31% 3R3R, 48% 2R3R, 21% 2R2R, 0.4% 2R6R, respectively.

The success rates for these assays were MTHFD1 1958G>A 99%, SHMT1 1420C>T 99.5%, TYMS 28 bp-repeat 99%, FPGS 114G>A 91.2%, FPGS 1994A>G 97.1%, GGH 452C>T 98.5%, and GGH 16T>C 94.1%.

All 17 SNP genotype frequencies showed Hardy-Weinberg equilibrium. The mean for overall success rate was 97.6%. The population consisted of 93.2% Caucasian (n=191), 2.4% Asian (n=5), 1.0% African (n=2), 3.4% other (n=3 Hindustani, n=3 Surinamese, n=1 Israeli).

Statistical Analysis

Variables between responders and non-responders were compared using the Student's t-test or Mann-Whitney U test or Chi-square test depending on the tested variable. Candidate variables with a p-value of $\leq 0.1$ were selected for the multiple prediction model. Except for CCP status, missing baseline values were not replaced; given the data were 98.6% complete. Missing CCP data were imputed, since the data were 85% complete (n=178). The unknown CCP status per patient was replaced by expected probability of a patient being CCP positive or negative given the Rf status.

Differences in genotype distribution for response were tested by two-by-two cross tabulations for carriers-versus-noncarriers analysis with a two-sided Chi-square test.

For continuous variables such as DAS, their contribution to MTX response was studied both as continuous and categorical variables in quartiles. On clinical grounds, the interaction between rheumatoid factor, smoking and CCP status was explored (13; 47). The interaction between age (<50 years, 50-60 years and >60 years) and gender was also studied (17).

In the backward selection procedure, the most significant independent variables were identified using p>0.10 as the removal criterion. This was done using both genetic and clinical candidate variables (the pharmacogenetic model) and only the clinical variables (the non-genetic model).

The predicted probability for MTX efficacy in a logistic regression model is related to the covariates in the equation $A+B1*x1+B2*x2+B3*x3\ldots Bk*xk$ (where A=the estimated constant term, x=a particular value for an explanatory variable and B=the regression coefficient). The exponential of the regression coefficient, $eB$, is an estimate of the adjusted odds ratio. The estimated probability for response was calculated for each individual patient with a set of variable values. A receiver-operating characteristic (ROC) curve was derived to evaluate the discriminative performance of the model. Cross-validation was performed to control for overfitting (48).

Weighted scores for the simplified model were assigned by rounding the regression coefficients in the final model to the nearest number ending in 0.5 or 0.0. Negative regression coefficients were inverted to obtain only positive weighted scores. Categories within a variable were grouped if regression coefficients led to identical scores. The calculated scores per individual were compared with the observed responses to MTX. Higher calculated scores reflect higher probability of non-response to MTX. Several clinical score cutoff levels that represent approximately >0.80 or <0.20 probability of response were chosen to classify patients as nonresponders, intermediate or responders. The true positive rate and true negative response rates were calculated. All statistical analyses were performed using SPSS 11.5 software (SPSS Inc., Chicago, Ill.).

Results

Univariate Analysis of Baseline Variables in Relation to MTX Monotherapy Efficacy Table 1 summarizes the comparison of baseline factors between responders and nonresponders. At 6 months of treatment with MTX, 47% of patients (n=87) were responders. Among these responders, 43% were receiving MTX 15 mg weekly and 57% were receiving MTX 25 mg weekly. Sixteen variables were selected for the multivariate analysis (p≦0.1). Prior to multivariate analysis, the interaction between Rf, smoking and CCP status was studied. In this context, patients were categorized into each possible Rf, smoking and CCP status combination. Data showed a difference in MTX response for the combined variable Rf and smoking status (p=0.088), but no difference (p>0.1) for combinations including CCP status and MTX efficacy. Accordingly, Rf positive and Rf negative patients were divided into 2 additional groups by smoking status. Between age and gender no significant interaction was found. However, gender and menopausal status were combined into a new variable with three categories based on a biological rationale: male, premenopausal female and postmenopausal female. Therefore, the total number of non-genetic variables selected for the multivariate analysis was 15.

Table 2 displays the comparison of wild type and/or mutant allele carriers for the de novo genotyped SNPs between responders and nonresponders. Only MTHFD1 1958A>G, which compared the G-allelic carriers versus the homozygous mutant AA genotypes, showed a difference between responders and nonresponders. In addition, 3 out of the 10 previously genotyped SNPs were associated with MTX good clinical response at 6 months. These SNPs were AMPD1 34C>T, ITPA 94C>A and ATIC 347C>G (20). Specifically, the AMPD1 34T-allele carriers, the ITPA CC genotyped and the ATIC 347 CC genotyped were more likely to achieve good clinical response. Thus, 4 SNPs were selected for the subsequent multivariate analysis.

Multivariate Analysis of Baseline Variables in Relation to MTX Monotherapy Efficacy The independent predicting variables resulting from stepwise selection procedure were gender; Rf status; smoking; DAS at baseline; SJC; HAQ; and 4 polymorphisms in AMPD1, ATIC, ITPA and MTHFD1 genes. Since the SJC is a composite measure of the DAS, there is a large correlation between these two variables. Adding DAS at baseline and SJC variables in the model yielded, due to colinearity, coefficients which are difficult to interpret. The HAQ also showed coefficients which are difficult to interpret. This is likely to be due to the strong correlations between HAQ and DAS as described previously (49). These coefficients did not allow HAQ and SJC to be entered simultaneously with DAS at baseline in the model.

Therefore, the definite model to obtain a simple pharmacogenetic score for MTX monotherapy efficacy consisted of the independent variables gender, Rf status, smoking status, DAS at baseline and 4 polymorphisms in the AMPD1, ATIC, ITPA and MTHFD1 genes. All factors were significantly (p<0.05) associated with MTX response at 6 months, and the model had an explained variance (Cox and Snell R2) of 35%.

Validity and Predictive Value of the Clinical Pharmacogenetic Model for MTX Monotherapy Efficacy The predicted probability varied between 0.012 and 0.994 in our population, reflecting the probability of response to MTX (0=responder, 1=non-responder). The probability of response was converted into a simplified clinical score. The regression coefficients of the logistic regression model and the assigned points per variable for the simplified prediction are listed in Table 3. The scores in our population ranged between 0 and 9.5, with a lower score reflecting a higher probability of response to MTX. The cutoff values were set at ≦3.5 points for responders and ≧6 points for nonresponders. The score of ≦3.5 had a true positive rate of 95%. The true positive rate reflects the proportion of patients with a high probability for MTX efficacy that were true responders. A score of ≧6 had a true negative response rate of 86%. This reflects the proportion of patients with a low probability for MTX efficacy that were true nonresponders. The numbers of predicted and observed patients per response category are displayed in Table 4a. With the clinical pharmacogenetic model 60% (n=110) of patients were classified as responder or non-responder with baseline variables only.

As presented in FIG. 1, a ROC of the pharmacogenetic model was prepared. The discriminative ability of the model (area under the curve, AUC) was 85% (95% C.I 80%-91%). The cross-validation of the definite model resulted in a ROC for the prediction of MTX response of 79% (95% C.I. 73%-86%).

To improve the usefulness of the prediction of MTX monotherapy efficacy for this intermediate group, an additional parameter was introduced to patients with a score of >3.5 but <6 points n=74). It was studied whether a decrease in DAS of >1.2, 3 months after initiating MTX therapy could improve the classification of this group.

Selecting patients with a predicted intermediate probability of response to MTX showed that if patients achieved a DAS decrease of >1.2 at 3 months, the likelihood of achieving good clinical response at 6 months was 78% (31 patients out of 40; 95% CI 62-89%). The likelihood of being a non-responder was 76% (26 patients out of 34; 95% CI 59-89%) if patients had not achieved a decrease in DAS of >1.2 at 3 months.

Finally, therapy recommendations on the basis of the clinical pharmacogenetic model are suggested to assist initial treatment decisions. Table 5 displays the suggestions per response category.

Predictive Value of Non-Genetic Clinical Baseline Variables in Relation to MTX Monotherapy Efficacy To clarify whether pharmacogenetic testing adds an adequate amount of information in predicting MTX treatment response for all patients (e.g. for patients with favorable clinical phenotypes such as non-smoking status, negative Rf and a DAS of ≦3.8), a second predictive model excluding genetic variables was developed.

Using the identical selection procedure a non-genetic model consisting of the independent predicting variables gender, DAS at baseline and Rf status in combination with smoking was generated. To compare the discriminative ability of this non-genetic model with the pharmacogenetic model, a ROC was prepared (FIG. 1). The comparison of ROCs showed that the sensitivity and specificity are positively correlated with genetic information. The discriminative ability (AUC) of the non-genetic model was 79% (95% CL 72%-85%). However, this model categorized only 32% (n=60) of the patients as responder or non-responder (Table 4b). The explained variance (Cox and Snell R2) was 25%.

Replication of the Clinical Pharmacogenetic Model for MTX Monotherapy Efficacy

Thirty-eight patients were recruited to replicate the genetic model. The validation cohort data were collected after development of the predictive model, but the investigators were blinded to either the clinical parameters or the genotyping results for the replication group. Fourteen patients were available from the BeSt study; they were treated with initial MTX monotherapy, but DNA samples were obtained after the clinical pharmacogenetic model was developed. Twenty-four patients were available from the RA cohort of the rheumatology department at the University Medical Center Nijmegen (UMCN), consisting of 553 patients (5, 51). Patients were eligible for the replication cohort if they fulfilled the ACR 1987 criteria for RA, started with MTX monotherapy, had not been treated previously with DMARDs other than antimalarial agents, and had disease duration of less than 2 years. In addition, clinical data comprising the prediction model and DNA samples had to be available. In the UMCN cohort, 352 patients were recorded as having received MTX at any time point. Of these 352 patients, only 36 received MTX monotherapy as their primary DMARD for more than 6 months. Twenty-four of these 36 patients were used for validation of the clinical model; the other 12 patients were excluded because no DNA was available, poor quality DNA was available, or prednisone was prescribed as additional therapy in doses ≧10 mg.

in this cohort were women, and 62% were RF positive. No significant differences between the replication cohort and the BeSt population were observed for age, gender, RF status, and MTHFD, ATIC, AMPD, and ITPA genotype frequencies. The DAS at baseline in the replication cohort was 3.8, which was significantly lower than the DAS at baseline in the BeSt population (Table 1). The calculated simple scores in the replication group of RA patients ranged from 1 to 9. The true positive response rate for this cohort was 70% (7 of 10 patients; 95% CI 35-93%), and the true negative response rate was 72% (13 of 18 patients; 95% CI 47-90%). In addition, 28 patients (68%) were categorized as responders and nonresponders, whereas 10 patients (32%) were categorized as intermediate responders.

TABLE 1

Comparison Of Baseline Variables Between Responders And Nonresponders

| Baseline variable | Responders (n = 87) | Nonresponders (n = 99) | P-value |
|---|---|---|---|
| Demographic factors | | | |
| Age (mean, years)[sd] | 55.3 [14] | 53.6 [13] | 0.397 |
| Female gender (%) | 60 | 79 | 0.005 |
| Alcohol consumption (%) | 46 | 42 | 0.680 |
| Smoking (%) | 32 | 46 | 0.174 |
| Body mass index (mean)[sd] | 25.5 [3.8] | 26.3 [4.6] | 0.231 |
| Clinical factors | | | |
| DAS (mean)[sd] | 4.1 [0.9] | 4.7 [0.7] | <0.001 |
| SJC (median)[IQR] | 11 [8-18]] | 14 [11-20] | 0.007 |
| RAI (median)[IQR] | 11 [7-15] | 16 [13-20] | <0.001 |
| Duration of complaints in weeks (median)[IQR] | 24 [13-54] | 25 [15-42] | 0.757 |
| VAS for physician's assessment of disease activity (mean)[sd] | 53 [17] | 59 [17] | 0.028 |
| VAS for pain (mean)[sd] | 47 [22] | 55 [21] | 0.009 |
| VAS for patient's assessment of disease activity (mean)[sd] | 55 [23] | 62 [22] | 0.034 |
| VAS for patient's assessment of global health (mean)[sd] | 49 [19] | 54 [19] | 0.061 |
| VAS for morning stiffness (mean)[sd] | 55 [24] | 62 [22] | 0.058 |
| HAQ score (mean)[sd] | 1.20 [0.7] | 1.44 [0.6] | 0.008 |
| Biochemical and immunological factors | | | |
| ESR (mm/hr, median)[IQR] | 34 [18-50] | 40 [26-65] | 0.033 |
| CRP (mg/L, median)[IQR] | 20 [9-42] | 24 [14-58] | 0.072 |
| Rf positive (%) | 62 | 74 | 0.088 |
| CCP positive (%)* | 44 | 52 | 0.695 |
| Creatinine clearance (ml/min, mean)[sd] | 103 [29] | 107 [33] | 0.378 |
| Other health status factors | | | |
| NSAIDs use (%) | 100 | 100 | — |
| Co-morbidity (%)# | 33 | 48 | 0.050 |
| Female and postmenopausal status (%) | 39 | 55 | 0.017 |
| Hormone supplementation (%) | 28 | 18 | 0.046 |

VAS = visual analogue scale (0-100 mm);
CCP = anti-cyclic citrulline peptide;
DAS = disease activity score;
IQR = interquartiles range;
sd = standard deviation;
SJC = swollen joint count;
RAI = Ritchie Articular Index;
HAQ = Health Assessment Questionnaire;
ESR = erythrocyte sedimentation rate;
CRP = C-reactive protein;
Rf = rheumatoid factor;
ALAT = alanine aminotransferase enzymes;
NSAIDs = nonsteroidal anti-inflammatory drugs.
*CCP values were not determined at baseline (ref. methods section).
Co-morbidity was defined as the patient's use of other drug use than RA related drugs.

The response at 6 months after starting MTX treatment in the group of RA patients (n=38) in the replication model was 45% (n=17), with an average MTX dosage of 19 mg weekly (range 5-25 mg weekly). Seventy-one percent of the patients

TABLE 2

Comparison Of De Novo Typed Snps Between Responders And Nonresponders

| SNP Genotype | Responders (n = 87) | % | Nonresponders (n = 99) | % | P-value |
|---|---|---|---|---|---|
| MTHFD1 1958G > A | | | | | |
| GG vs. A-allele carriers | 35 | 65 | 24 | 76 | 0.101 |
| G-allele carriers vs. AA | 85 | 15 | 74 | 26 | 0.070 |
| SHMT1 1420C > T | | | | | |
| CC vs. T-allele carriers | 56 | 44 | 59 | 41 | 0.704 |
| C-allele carriers vs. TT | 94 | 6 | 98 | 2 | 0.177 |
| TYMS 28 bp-repeat | | | | | |
| 3R/3R vs. 2R-repeats carries | 33 | 67 | 26 | 74 | 0.321 |
| 3R-repeat carriers vs. 2R/2R | 78 | 22 | 80 | 20 | 0.749 |
| FPGS 114 G > A | | | | | |
| AA vs. G-allele carriers | 3 | 97 | 8 | 92 | 0.125 |
| A-allele carriers vs. GG | 48 | 52 | 49 | 51 | 0.638 |
| FPGS 1994A > G | | | | | |
| AA vs. G-allele carriers | 26 | 74 | 37 | 63 | 0.128 |
| A-allele carriers vs. GG | 75 | 25 | 81 | 19 | 0.362 |
| GGH 452C > T | | | | | |
| CC vs. T-allele carriers | 85 | 15 | 82 | 18 | 0.580 |
| C-allele carriers vs. TT | 100 | — | 100 | — | — |
| GGH 16T > C | | | | | |
| TT vs. C-allele carriers | 49 | 51 | 56 | 44 | 0.380 |
| T-allele carriers vs. CC | 93 | 7 | 91 | 9 | 0.705 |

MTHFD1 = methylenetetrahydrofolate dehydrogenase;
SHMT1 = serine hydroxymethyltransferase;
FPGS = folylpolyglutamate synthase;
GGH = gamma-glutamyl hydrolase;
TYMS = thymidylate synthetase.

|  | Predicted[#] | | |
|---|---|---|---|
| Observed response[$] | Non-responder | Intermediate | Responder |
| Non-responder | 62 | 35 | 2 |
| Responder | 10 | 39 | 36 |

[$]Nonresponders were defined as patients with a DAS of >2.4 with MTX therapy at 6 months, responders were defined as patients with a DAS of ≦2.4 with MTX therapy at 6 months
[#]Nonresponders defined as prediction derived score ≧6, intermediate responders defined as predicting derived score >3.5, but <6. Responders defined as prediction derived score ≦3.5. Cutoff levels were chosen based on the clinical score which represent probabilities of response to MTX of approximately >0.80 and <0.20. Two patients are missing since their genotyping was incomplete.

TABLE 4B

Non-Genetic Model; Number Of Observed And Predicted Patients With Or Without Mtx Monotherapy Response At 6 Months

|  | Predicted[*] | | |
|---|---|---|---|
| Observed response[$] | Non-responder | Intermediate | Responder |
| Non-responder | 23 | 72 | 4 |
| Responder | 2 | 54 | 31 |

[$]Nonresponders were defined as patients with a DAS of >2.4 with MTX therapy at 6 months, responders were defined as patients with a DAS of ≦2.4 with MTX therapy at 6 months.
[*]Number of predicted nonresponders and responders through the non-genetic model with independent predicting variables gender, DAS at baseline and Rf status in combination with smoking. Cutoff levels were chosen based on the clinical score which represent probabilities of response to MTX of approximately >0.80 and <0.20.

TABLE 5

Recommendations For The Clinical Application Of The Simple Score To Select Patients Eligible For Mtx Monotherapy

| Categories | Clinical consequence |
|---|---|
| Scores ≧6 | Low probability of response to MTX |

TABLE 3

Derived Scores, Regression Coefficient Values And Odds Ratios Of Baseline Variables To Predict Mtx Monotherapy Efficacy At 6 Months

| Baseline Variable | Value | | Score[*] | B | OR (95% C.I.) |
|---|---|---|---|---|---|
| Gender | Female premenopausal | | 1 | −1.2 | 0.3 (0.1-0.9) |
|  | postmenopausal | | 1 | −0.79 | 0.5 (0.2-1.1) |
|  | Male | | 0 | — | — |
| Disease activity | DAS at baseline ≦3.8 | | 0 | — | — |
|  | DAS at baseline >3.8, but ≦5.1 | 2nd quartile | 3 | −2.8 | 0.1 (0.0-0.2) |
|  |  | 3rd quartile | 3 | −2.7 | 0.1 (0.0-0.3) |
|  | DAS at baseline >5.1 | | 3.5 | −3.4 | 0.1 (0.0-0.1) |
| Immunol. factors | RF negative and non-smoker | | 0 | — | — |
|  | RF negative and smoker | | 1 | −0.80 | 0.5 (0.1-1.8) |
|  | RF positive and non-smoker | | 1 | −0.75 | 0.5 (0.2-1.2) |
|  | RF positive and smoker | | 2 | −2.2 | 0.1 (0.0-0.4) |
| Genetic factors | MTHFD1 1958 AA genotype | | 1 | −0.98 | 0.4 (0.2-1.0) |
|  | a) AMPD1 34 CC genotype | | 1 | −1.2 | 0.3 (0.1-0.7) |
|  | b) ITPA 94 A-allele carrier | | 2 | −1.7 | 0.2 (0.1-0.6) |
|  | ATIC 347 G-allele carrier | | 1 | −1.1 | 0.4 (0.2-0.8) |
|  | Other genotypes | | 0 | — | — |

B = regression coefficient in the definite model;
OR = odds ratio;
95% C.I. = 95% confidence interval;
MTHFD1 = methylenetetrahydrofolate dehydrogenase;
AMPD1 = adenosine monophosphate deaminase;
ATIC = aminoimidazole carboxamide ribonucleotide transformylase;
ITPA = inosine triphosphate pyrophosphatase.
[*]Higher scores represent higher probability of non-response to MTX.

TABLE 4A

Pharmacogenetic Model; Number Of Observed And Predicted Patients With Or Without Mtx Monotherapy Response At 6 Months

| | |
|---|---|
| | monotherapy, consider a different DMARD or choose a combination strategy; |
| Scores <6, but >3.5 | Intermediate probability of response to MTX monotherapy; start MTX monotherapy 15 mg weekly and evaluate at 3 months; A. If a decrease in DAS of more than 1.2, continue MTX monotherapy but increase the dosage to 25 mg weekly; B. If a decrease in DAS of 1.2 or less, consider a different DMARD or a combination strategy. |
| Scores ≦3.5 | Start MTX monotherapy 15 mg weekly, if necessary (DAS >2.4) increase the dosage after 3 months to 25 mg weekly. |

REFERENCES (1) Welsing P M, Landewe R B, van Riel P L, Boers M, van Gestel A M, van der L S et al. The relationship between disease activity and radiologic progression in patients with rheumatoid arthritis: a longitudinal analysis. *Arthritis Rheum.* 2004; 50(7):2082-2093.

(2) Mottonen T, Hannonen P, Korpela M, Nissila M, Kautiainen H, Ilonen J et al. Delay to institution of therapy and induction of remission using single-drug or combination-disease-modifying antirheumatic drug therapy in early rheumatoid arthritis. *Arthritis Rheum.* 2002; 46(4):894-898.

(3) Mottonen T, Hannonen P, Leirisalo-Repo M, Nissila M, Kautiainen H, Korpela M et al. Comparison of combination therapy with single-drug therapy in early rheumatoid arthritis: a randomized trial. FIN-RACo trial group. *Lancet* 1999; 353(9164):1568-1573.

(4) Landewe R B, Boers M, Verhoeven A C, Westhovens R, van de Laar M A, Markusse H M et al. COBRA combination therapy in patients with early rheumatoid arthritis: long-term structural benefits of a brief intervention. *Arthritis Rheum.* 2002; 46(2):347-356.

(5) Goekoop-Ruiterman Y P, Vries-Bouwstra J K, Allaart C F, van Zeben D, Kerstens P J, Hazes J M et al. Clinical and radiographic outcomes of four different treatment strategies in patients with early rheumatoid arthritis (the BeSt study): a randomized, controlled trial. *Arthritis Rheum.* 2005; 52(11):3381-3390.

(6) Matteson E L, Weyand C M, Fulbright J W, Christianson T J H, McClelland R L, Goronzy J J. How aggressive should initial therapy for rheumatoid arthritis be? Factors associated with response to 'non-aggressive' DMARD treatment and perspective from a 2-yr open label trial. *Rheumatology* 2004; 43(5):619-625.

(7) Scott D L. Evidence for early disease-modifying drugs in rheumatoid arthritis. *Arthritis Research & Therapy* 2004; 6(1):15-18.

(8) Bongartz T, Sutton A J, Sweeting M J, Buchan I, Matteson E L, Montori V. Anti-TNF antibody therapy in rheumatoid arthritis and the risk of serious infections and malignancies: systematic review and meta-analysis of rare harmful effects in randomized controlled trials. *JAMA* 2006; 295 (19):2275-2285.

(9) van Everdingen A A, Jacobs J W, Siewertsz Van Reesema D R, Bijlsma J W. Low-dose prednisone therapy for patients with early active rheumatoid arthritis: clinical efficacy, disease-modifying properties, and side effects: a randomized, double-blind, placebo-controlled clinical trial. *Ann. Intern Med.* 2002; 136(1): 1-12.

(10) Green M, Marzo-Ortega H, McGonagle D, Wakefield R, Proudman S, Conaghan P et al. Persistence of mild, early inflammatory arthritis: the importance of disease duration, rheumatoid factor, and the shared epitope. *Arthritis Rheum,* 1999; 42(10):2184-2188.

(11) Tengstrand B, Ahlmen M, Hafstrom I. The influence of sex on rheumatoid arthritis: a prospective study of onset and outcome after 2 years. *J. Rheumatol* 2004; 31(2):214-222.

(12) Morel J, Combe B. How to predict prognosis in early rheumatoid arthritis. *Best Bract Res. Clin. Rheumatol* 2005; 19(1):137-146.

(13) Rantapaa-Dahlqvist S, de Jong B A, Berglin E, Hallmans G, Wadell G, Stenlund H et al. Antibodies against cyclic citrullinated peptide and IgA rheumatoid factor predict the development of rheumatoid arthritis. *Arthritis Rheum.* 2003; 48(10):2741-2749.

(14) Criswell L A, Lum R F, Turner K N, Woehl B, Zhu Y, Wang J et al. The influence of genetic variation in the HLA-DRB1 and LTA-TNF regions on the response to treatment of early rheumatoid arthritis with methotrexate or etanercept. *Arthritis Rheum.* 2004; 50(9):2750-2756.

(15) Gossec L, Dougados M, Goupille P, Cantagrel A, Sibilia J, Meyer O et al. Prognostic factors for remission in early rheumatoid arthritis: a multiparameter prospective study. *Ann. Rheum. Dis.* 2004; 63(6):675-680.

(16) Anderson J J, Wells G, Verhoeven A C, Felson D T. Factors predicting response to treatment in rheumatoid arthritis: the importance of disease duration. *Arthritis Rheum.* 2000; 43(1):22-29.

(17) Symmons D P. Environmental factors and the outcome of rheumatoid arthritis. *Best Pract. Res. Clin. Rheumatol.* 2003; 17(5):717-727.

(18) Symmons D P. Epidemiology of rheumatoid arthritis: determinants of onset, persistence and outcome. *Best Pract. Res. Clin. Rheumatol.* 2002; 16(5):707-722.

(19) Wessels J A, Vries-Bouwstra J K, Heijmans B T, Slagboom P E, Goekoop-Ruiterman Y P, Allaart C F et al. Efficacy and toxicity of methotrexate in early rheumatoid arthritis are associated with single-nucleotide polymorphisms in genes coding for folate pathway enzymes. *Arthritis Rheum.* 2006; 54(4):1087-1095.

(20) Wessels J. A. M., Kooloos W M, De Jonge R, De Vries-Bouwstra J K, Allaart C F, Linssen A, Collee C G, De Sonnaville P, Lindemans, J, Huizinga, T W, Guchelaar H J. Relationship between genetic variants in the adenosine pathway and outcome of methotrexate treatment in patients with recent-onset rheumatoid arthritis. *Arthritis Rheum.* 2006 September; 54(9):2830-2839.

(21) Dervieux T, Furst D, Lein D O, Capps R, Smith K, Walsh M et al. Polyglutamation of methotrexate with common polymorphisms in reduced folate carrier, aminoimidazole carboxamide ribonucleotide transformylase, and thymidylate synthase are associated with methotrexate effects in rheumatoid arthritis. *Arthritis Rheum.* 2004; 50(9):2766-2774.

(22) Hoekstra M, van Ede A E, Haagsma C J, van de Laar M A, Huizinga T W, Kruijsen M W et al. Factors associated with toxicity, final dose, and efficacy of methotrexate in patients with rheumatoid arthritis. *Ann. Rheum. Dis.* 2003; 62(5):423-426.

(23) Arnett F C, Edworthy S M, Bloch D A, McShane D J, Fries J F, Cooper N S et al. The American Rheumatism Association 1987 revised criteria for the classification of rheumatoid arthritis. *Arthritis Rheum.* 1988; 31(3):315-324.

(24) van Gestel A M, Prevoo M L, 't Hof M A, van Rijswijk M H, van de Putte L B, van Riel P L. Development and validation of the European League Against Rheumatism response criteria for rheumatoid arthritis. Comparison with

(24) the preliminary American College of Rheumatology and the World Health Organization/International League Against Rheumatism Criteria. *Arthritis Rheum.* 1996; 39(1):34-40.

(25) van der Heijde D M, van't H M, van Riel P L, van de Putte L B. Development of a disease activity score based on judgment in clinical practice by rheumatologists. *J. Rheumatol.* 1993; 20(3):579-581.

(26) Felson D T, Anderson J J, Boers M, Bombardier C, Chernoff M, Fried B et al. The American College of Rheumatology preliminary core set of disease activity measures for rheumatoid arthritis clinical trials. The Committee on Outcome Measures in Rheumatoid Arthritis Clinical Trials. *Arthritis Rheum.* 1993; 36(6):729-740.

(27) Ronnelid J, Wick M C, Lampa J, Lindblad S, Nordmark B, Klareskog L et al. Longitudinal analysis of citrullinated protein/peptide antibodies (anti-CP) during 5 year follow up in early rheumatoid arthritis: anti-CP status predicts worse disease activity and greater radiological progression. *Ann. Rheum. Dis.* 2005; 64(12):1744-1749.

(28) Ulrich C M, Robien K, Sparks R. Pharmacogenetics and folate metabolism—a promising direction. *Pharmacogenomics* 2002; 3(3):299-313.

(29) Krajinovic M, Moghrabi A. Pharmacogenetics of methotrexate. *Pharmacogenomics* 2004; 5(7):819-834.

(30) Cronstein B N. Low-dose methotrexate: a mainstay in the treatment of rheumatoid arthritis. *Pharmacol Rev.* 2005; 57(2):163-172.

(31) Huizinga T W, Pisetsky D S, Kimberly R P. Associations, populations, and the truth: recommendations for genetic association studies in Arthritis & Rheumatism. 38. *Arthritis Rheum.* 2004; 50(7):2066-2071.

(32) Hattersley A T, McCarthy M I. What makes a good genetic association study? 2. *Lancet* 2005; 366(9493): 1315-1323.

(33) Marie S, Heron B, Bitoun P, Timmerman T, Van Den B G, Vincent M F. AICA-ribosiduria: a novel, neurologically devastating inborn error of purine biosynthesis caused by mutation of ATIC. *Am. J. Hum. Genet.* 2004; 74(6):1276-1281.

(34) Cao H, Hegele R A. DNA polymorphisms in ITPA including basis of inosine triphosphatase deficiency. *J. Hum. Genet.* 2002; 47(11):620-622.

(35) Marinaki A M, Ansari A, Duley J A, Arenas M, Sumi S, Lewis C M et al. Adverse drug reactions to azathioprine therapy are associated with polymorphism in the gene encoding inosine triphosphate pyrophosphatase (ITPase). *Pharmacogenetics* 2004; 14(3):181-187.

(36) Weisman M H, Furst D E, Park G S, Kremer J M, Smith K M, Wallace D J et al. Risk genotypes in folate-dependent enzymes and their association with methotrexate-related side effects in rheumatoid arthritis. *Arthritis Rheum.* 2006; 54(2):607-612.

(37) Kohlmeier M, da Costa K A, Fischer L M, Zeisel S H. Genetic variation of folate-mediated one-carbon transfer pathway predicts susceptibility to choline deficiency in humans. *Proc. Natl. Acad. Sci. U.S.A.* 2005; 102(44): 16025-16030.

(38) Skibola C F, Smith M T, Hubbard A, Shane B, Roberts A C, Law G R et al. Polymorphisms in the thymidylate synthase and serine hydroxymethyltransferase genes and risk of adult acute lymphocytic leukemia. *Blood* 2002; 99(10): 3786-3791.

(39) Chave K J, Ryan T J, Chmura S E, Galivan J. Identification of single nucleotide polymorphisms in the human gamma-glutamyl hydrolase gene and characterization of promoter polymorphisms. *Gene* 2003; 319:167-175.

(40) Kalsi A K, Yuen A H, Rybakowska I M, Johnson P H, Slominska F, Birks E J et al. Decreased cardiac activity of AMP deaminase in subjects with the AMPD1 mutation—a potential mechanism of protection in heart failure. *Cardiovasc. Res.* 2003; 59(3):678-684.

(41) Gaughan D J, Kluijtmans L A, Barbaux S, McMaster D, Young I S, Yarnell J W et al. The methionine synthase reductase (MTRR) A66G polymorphism is a novel genetic determinant of plasma homocysteine concentrations. *Atherosclerosis* 2001; 157(2):451-456.

(42) Dervieux T, Kremer J, Lein D O, Capps R, Barham R., Meyer G et al. Contribution of common polymorphisms in reduced folate carrier and gamma-glutamylhydrolase to methotrexate polyglutamate levels in patients with rheumatoid arthritis. *Pharmacogenetics* 14, 733-739. 2004. Ref Type: Generic

(43) Bosco P, Gueant-Rodriguez R M, Anello G, Barone C, Namour F, Caraci F et al. Methionine synthase (MTR) 2756 (A→G) polymorphism, double heterozygosity methionine synthase 2756 AG/methionine synthase reductase (MTRR) 66 AG, and elevated homocysteinemia are three risk factors for having a child with Down syndrome. *Am. J. Med. Genet. A* 2003; 121(3):219-224.

(44) Stranzl T, Wolf J, Leeb B F, Smolen J S, Pirker R, Filipits M. Expression of folylpolyglutamyl synthetase predicts poor response to methotrexate therapy in patients with rheumatoid arthritis. *Clin. Exp. Rheumatol.* 2003; 21(1): 27-32.

(45) Cheng Q, Wu B, Kager L, Panetta J C, Zheng J, Pui C H et al. A substrate specific functional polymorphism of human gamma-glutamyl hydrolase alters catalytic activity and methotrexate polyglutamate accumulation in acute lymphoblastic leukaemia cells. *Pharmacogenetics* 2004; 14(8):557-567.

(46) Morisaki T, Gross M, Morisaki H, Pongratz D, Zollner N, Holmes E W. Molecular basis of AMP deaminase deficiency in skeletal muscle. *Proc. Natl. Acad. Sci. U.S.A.* 1992; 89(14):6457-6461.

(47) Klareskog L, Stolt P, Lundberg K, Kallberg H, Bengtsson C, Grunewald J et al. A new model for an etiology of rheumatoid arthritis: smoking may trigger HLA-DR (shared epitope)-restricted immune reactions to autoantigens modified by citrullination. *Arthritis Rheum.* 2006; 54(1): 38-46.

(48) Harrell F E, Jr., Lee K L, Mark D B. Multivariable prognostic models: issues in developing models, evaluating assumptions and adequacy, and measuring and reducing errors. *Stat. Med.* 1996; 15(4):361-387.

(49) Drossaers-Bakker K W, de Buck M, van Zeben D, Zwinderman A H, Breedveld F C, Hazes J M. Long-term course and outcome of functional capacity in rheumatoid arthritis: the effect of disease activity and radiologic damage over time. *Arthritis Rheum.* 1999; 42(9):1854-1860.

(50) Hughes L B, Beasley T M, Patel H, Tiwari H K, Morgan S L, Baggott J E et al. Racial/Ethnic Differences in Allele Frequencies of Single Nucleotide Polymorphisms in the Methylenetetrahydrofolate Reductase Gene and Their Influence on Response to Methotrexate in Rheumatoid Arthritis. *Ann. Rheum. Dis.* 2006.

(51) Welsing P M, van Riel P L. The Nijmegen Inception Cohort of Early Rheumatoid Arthritis. *J. Rheurmatol. Suppl.* 2004; 69:14-21.

What is claimed is:

1. A method for determining clinical responsiveness to antifolate therapy in a human subject afflicted with, or at risk of developing, arthritis comprising detecting the presence in a biological sample from the subject of a 1958G>A polymorphism in the methylenetetrahydrofolate dehydrogenase (MTHFD1) gene, a 34C>T polymorphism in the adenosine monophosphate deaminase (AMPD1) gene, a 347 C>G polymorphism in the aminoimidazole carboxamide ribonucleotide transformylase (ATIC) gene; and a 94 C>A polymorphism in the inosine triphosphate pyrophosphatase (ITPA) gene, wherein the presence of the polymorphisms in the biological sample is indicative of clinical responsiveness to the antifolate therapy.

2. The method according to claim 1, wherein the polymorphisms are detected by a technique selected from the group consisting of microarray analysis, DNA sequencing or allele specific PCR techniques.

3. The method according to claim 1, wherein the method further comprises the step of:
    a) determining the clinical responsiveness to the antifolate therapy by correlating the presence of the polymorphisms with a predefined responsiveness value associated with each particular polymorphism.

4. The method according to claim 3, wherein a responsiveness score is calculated as the sum of the responsiveness values for each polymorphism.

5. The method according to claim 3, wherein the method further comprises the step of:
    b) determining a set of clinical parameter values comprising at least one of:
        i) the gender of the subject and optionally the pre- or postmenopausal status of a female subject;
        ii) DAS at baseline, wherein DAS is disease activity score as defined by the European League Against Rheumatism;
        iii) the presence or absence of Rheumatoid factor; and,
        iv) smoking status; and,
    c) determining the clinical responsiveness to the antifolate therapy by correlating the values determined in steps a) and b) with a predefined responsiveness value associated with each particular polymorphism and parameter value.

6. The method according to claim 5, wherein a responsiveness score is calculated as the sum of the responsiveness values for each polymorphism and for each parameter value.

7. The method according to claim 6, wherein the responsiveness values assigned to the respective polymorphisms and parameter values are defined as between 50% and 150% of the values in a)-i):

a) 0 for male gender; 1 for female gender;
b) 0 for DAS at baseline<3.8;
   2.8 for DAS at baseline>3.8, but <5.1;
   3.4 for DAS at baseline>5.1;
c) 0 for Rheumatoid factor negative and non-smoker;
   0.8 for Rheumatoid factor negative and smoker;
   0.75 for Rheumatoid factor positive and non-smoker;
   2.2 for Rheumatoid factor positive and smoker;
d) 0.98 for MTHFD1 1958 AA genotype;
e) 1.2 for AMPD1 34 CC genotype;
f) 1.7 for ITPA A-allele carrier;
h) 1.1 for ATIC 347 G-allele carrier; and,
i) 0 for other genotypes;
and whereby the maximum responsiveness score is 11.5.

8. The method according to claim 7, wherein the responsiveness values assigned to the respective polymorphisms and parameter values are:
a) 0 for male gender; 1 for female gender;
b) 0 for DAS at baseline<3.8;
   3 for DAS at baseline>3.8, but <5.1;
   3.5 for DAS at baseline>5.1;
c) 0 for Rheumatoid factor negative and non-smoker;
   1 for Rheumatoid factor negative and smoker;
   1 for Rheumatoid factor positive and non-smoker;
   2 for Rheumatoid factor positive and smoker;
d) 1 for MTHFD1 1958 AA genotype;
e) 1 for AMPD1 34 CC genotype;
f) 2 for ITPA A-allele carrier;
h) 1 for A TIC 347 G-allele carrier; and,
i) 0 for other genotypes.

9. The method according to claim 7, wherein a responsiveness score of a subject of 6 or more indicates that the subject is not responsive to antifolate therapy.

10. The method according to claim 9, wherein a responsiveness score of a subject of more than 3.5 but less than 6 indicates that the subject has an intermediate responsiveness to antifolate therapy.

11. The method according to claim 1, wherein the subject is a subject with recent onset undifferentiated arthritis.

12. The method according to claim 1, wherein said antifolate is methotrexate.

13. A computer comprising a processor and memory, the processor being arranged to read from said memory and write into said memory, the memory comprising data and instructions arranged to provide said processor with the capacity to perform a method of determining a predicted responsiveness of a human subject to antifolate therapy, wherein the method comprises the steps of:
    a) determining for the subject the polymorphisms as defined in claim 1;

b) determining for the subject one or more of clinical parameter values for the individual comprising:
  i) the gender of the subject and optionally the pre- or postmenopausal status of a female subject;
  ii) DAS at baseline, wherein DAS is disease activity score as detected by the European League Against Rheumatism;
  iii) the presence or absence of Rheumatoid factor; and, smoking status; and,
c) determining the predicted responsiveness of a subject to antifolate therapy by correlating the parameter values determined in steps a) and b) with a predefined responsiveness value associated with each particular parameter value.

14. The computer according to claim 13, wherein the computer has an input connected to a sample analyzer for receiving analysis data signals of a biological sample, and wherein the processor is arranged for determining from said analysis data signals: i) the polymorphisms as defined in any one of claim 1; and, ii) the presence or absence of Rheumatoid factor.

15. The computer according to claim 13, wherein the processor is arranged for calculating a responsiveness score as the sum of the responsiveness values for each parameter value.

16. A sample analyzer comprising a computer in accordance with claim 13.

17. A non-transitory computer program product comprising data and instructions and arranged to be loaded in a memory of a computer, the data and instructions being arranged to provide said computer with the capacity to perform a method of determining a predicted responsiveness of a subject to antifolate therapy, wherein the method comprises the steps of:
  a) determining for the subject the polymorphisms as defined in claim 1;
  b) determining for the subject one or more of clinical parameter values for the individual comprising:
    i) the gender of the subject and optionally the pre- or postmenopausal status of a female subject;
    ii) DAS at baseline, wherein DAS is disease activity score as defined by the European League Against Rheumatism;
    iii) the presence or absence of Rheumatoid factor; and,
    iv) smoking status; and,
  c) determining the predicted responsiveness of a human subject to antifolate therapy by correlating the parameter values determined in steps a) and b) with a predefined responsiveness value associated with each particular parameter value.

18. A system for determining a predicted responsiveness of a human subject to antifolate therapy, the system comprising:
  a) a blood sample analyzer configured to analyze a blood sample provided by the subject and determine the polymorphisms as defined in claim 1, and an indicator of a presence or absence of Rheumatoid factor in a blood sample from the subject; and,
  b) a computing device configured to assign a responsiveness value to each of the indicators determined by the blood sample analyzer, wherein the computing device accesses data stored in a memory associating ranges of values for each of the indicators with respective responsiveness values, the computing device further configured to determine a predicted responsiveness of the subject to antifolate therapy based at least partly on the assigned responsiveness values.

19. The system according to claim 18, wherein the blood sample analyzer is located remote from the computing device.

20. The system according to claim 18, wherein the indicators are transmitted to the computing device via a network communication link.

21. The system according to claim 18, wherein the blood sample analyzer is located proximate the computing device.

22. The system according to claim 18, wherein the computing device is further configured to transmit one or more electronic messages indicating the determined predicted responsiveness.

23. The system according to claim 18, wherein the computing device receives the indicators via a web interface in data communication with the computing device.

24. The system of claim 18, wherein the computing device is further configured to assign a risk value to indicators indicating at least one of: i) the gender of the subject and optionally the pre- or postmenopausal status of a female subject; ii) DAS at baseline, wherein DAS is disease activity score as defined by the European League Against Rheumatism; and, iii) smoking status.

25. The method of claim 12, wherein the subject has recent onset undifferentiated arthritis.

26. The method according to claim 25, wherein the method further comprises the step of:
  a) determining the clinical responsiveness to the methotrexate therapy by correlating the presence of the polymorphisms with a predefined responsiveness value associated with each particular polymorphism.

27. The method according to claim 25, wherein a responsiveness score is calculated as the sum of the responsiveness values for each polymorphism.

28. The method according to claim 26, wherein the method further comprises the step of:
  b) determining a set of clinical parameter values comprising at least one of:
    i) the gender of the subject and optionally the pre- or postmenopausal status of a female subject;
    ii) DAS at baseline, wherein DAS is disease activity score as defined by the European League Against Rheumatism;
    iii) the presence or absence of Rheumatoid factor; and,
    iv) smoking status; and,
  c) determining the clinical responsiveness to the methotrexate therapy by correlating the values determined in steps a) and b) with a predefined responsiveness value associated with each particular polymorphism and parameter value.

29. The method according to claim 28, wherein a responsiveness score is calculated as the sum of the responsiveness values for each polymorphism and for each parameter value.

30. The method according to claim 29, wherein the responsiveness values assigned to the respective polymorphisms and parameter values are defined as between 50% and 150% of the values in a)-i):
  a) 0 for male gender; 1 for female gender;
  b) 0 for DAS at baseline<3.8;
    2.8 for DAS at baseline>3.8, but <5.1;
    3.4 for DAS at baseline>5.1;
  c) 0 for Rheumatoid factor negative and non-smoker;
    0.8 for Rheumatoid factor negative and smoker;
    0.75 for Rheumatoid factor positive and non-smoker;
    2.2 for Rheumatoid factor positive and smoker;
  d) 0.98 for MTHFD1 1958 AA genotype;
  e) 1.2 for AMPD1 34 CC genotype;
  f) 1.7 for ITPA A-allele carrier;

h) 1.1 for ATIC 347 G-allele carrier; and,
i) 0 for other genotypes;
and whereby the maximum responsiveness score is 11.5.

31. The method according to claim 30, wherein the responsiveness values assigned to the respective polymorphisms and parameter values are:
a) 0 for male gender; 1 for female gender;
b) 0 for DAS at baseline<3.8;
   3 for DAS at baseline>3.8, but <5.1;
   3.5 for DAS at baseline>5.1;
c) 0 for Rheumatoid factor negative and non-smoker;
   1 for Rheumatoid factor negative and smoker;
   1 for Rheumatoid factor positive and non-smoker;
   2 for Rheumatoid factor positive and smoker;
d) 1 for MTHFD1 1958 AA genotype;
e) 1 for AMPD1 34 CC genotype;
f) 2 for ITPA A-allele carrier;
h) 1 for A TIC 347 G-allele carrier; and,
i) 0 for other genotypes.

32. The method according to claim 30, wherein a responsiveness score of a subject of 6 or more indicates that the subject is not responsive to methotrexate therapy.

33. The method according to claim 32, wherein a responsiveness score of a subject of more than 3.5 but less than 6 indicates that the subject has an intermediate responsiveness to methotrexate therapy.

* * * * *

UNITED STATES PATENT AND TRADEMARK OFFICE
CERTIFICATE OF CORRECTION

PATENT NO. : 8,073,630 B2
APPLICATION NO. : 11/846406
DATED : December 6, 2011
INVENTOR(S) : Hendrik Jan Guchelaar and Tom Willem Johannes Huizinga It is certified that error appears in the above-identified patent and that said Letters Patent is hereby corrected as shown below:

On the title page item (73),

Please Delete "Exagen Diagnostics, Inc. Albuquerque, NM (US) and Replace with:

Academisch Zeikenhuis H.O.D.N. LUMC, Leiden, Netherlands (NL)

Signed and Sealed this
Twentieth Day of March, 2012

David J. Kappos
*Director of the United States Patent and Trademark Office*

UNITED STATES PATENT AND TRADEMARK OFFICE
CERTIFICATE OF CORRECTION

PATENT NO. : 8,073,630 B2
APPLICATION NO. : 11/846406
DATED : December 6, 2011
INVENTOR(S) : Hendrik Jan Guchelaar and Tom Willem Johannes Huizinga It is certified that error appears in the above-identified patent and that said Letters Patent is hereby corrected as shown below:

On the title page item (73),

Please Delete "Exagen Diagnostics, Inc. Albuquerque, NM (US)" and Replace with:

Academisch Ziekenhuis H.O.D.N. LUMC, Leiden, Netherlands (NL)

This certificate supersedes the Certificate of Correction issued March 20, 2012.

Signed and Sealed this
Fifteenth Day of May, 2012

David J. Kappos
*Director of the United States Patent and Trademark Office*

SEQUENCE LISTING

<160> NUMBER OF SEQ ID NOS: 4

<210> SEQ ID NO 1
<211> LENGTH: 476
<212> TYPE: PRT
<213> ORGANISM: Homo sapiens

<400> SEQUENCE: 1

```
Ile Asp Ala Arg Ile Phe His Glu Leu Thr Gln Thr Asp Lys Ala Leu
1               5                   10                  15

Phe Asn Arg Leu Val Pro Ser Val Asn Gly Val Arg Arg Phe Ser Asp
            20                  25                  30

Ile Gln Ile Arg Arg Leu Lys Arg Leu Gly Ile Glu Lys Thr Asp Pro
        35                  40                  45

Thr Thr Leu Thr Asp Glu Glu Ile Asn Arg Phe Ala Arg Leu Asp Ile
    50                  55                  60

Asp Pro Glu Thr Ile Thr Trp Gln Arg Val Leu Asp Thr Asn Asp Arg
65                  70                  75                  80

Phe Leu Arg Lys Ile Thr Ile Gly Gln Ala Pro Thr Glu Lys Gly His
                85                  90                  95

Thr Arg Thr Ala Gln Phe Asp Ile Ser Val Ala Ser Glu Ile Met Ala
            100                 105                 110

Val Leu Ala Leu Thr Thr Ser Leu Glu Asp Met Arg Glu Arg Leu Gly
        115                 120                 125

Lys Met Val Val Ala Ser Ser Lys Lys Gly Glu Pro Val Ser Ala Glu
    130                 135                 140

Asp Leu Gly Val Ser Gly Ala Leu Thr Val Leu Met Lys Asp Ala Ile
145                 150                 155                 160

Lys Pro Asn Leu Met Gln Thr Leu Glu Gly Thr Pro Val Phe Val His
                165                 170                 175

Ala Gly Pro Phe Ala Asn Ile Ala His Gly Asn Ser Ser Ile Ile Ala
            180                 185                 190

Asp Arg Ile Ala Leu Lys Leu Val Gly Pro Glu Gly Phe Val Val Thr
        195                 200                 205

Glu Ala Gly Phe Gly Ala Asp Ile Gly Met Glu Lys Phe Phe Asn Ile
    210                 215                 220

Lys Cys Arg Tyr Ser Gly Leu Cys Pro His Val Val Leu Val Ala
225                 230                 235                 240

Thr Val Arg Ala Leu Lys Met His Gly Gly Pro Thr Val Thr Ala
                245                 250                 255

Gly Leu Pro Leu Pro Lys Ala Tyr Ile Gln Glu Asn Leu Glu Leu Val
            260                 265                 270

Glu Lys Gly Phe Ser Asn Leu Lys Lys Gln Ile Glu Asn Ala Arg Met
        275                 280                 285

Phe Gly Ile Pro Val Val Val Ala Val Asn Ala Phe Lys Thr Asp Thr
    290                 295                 300

Glu Ser Glu Leu Asp Leu Ile Ser Arg Leu Ser Arg Glu His Gly Ala
305                 310                 315                 320

Phe Asp Ala Val Lys Cys Thr His Trp Ala Glu Gly Gly Lys Gly Ala
                325                 330                 335

Leu Ala Leu Ala Gln Ala Val Gln Arg Ala Ala Gln Ala Pro Ser Ser
            340                 345                 350

Phe Gln Leu Leu Tyr Asp Leu Lys Leu Pro Val Glu Asp Lys Ile Arg
        355                 360                 365
```

```
Ile Ile Ala Gln Lys Ile Tyr Gly Ala Asp Asp Ile Glu Leu Leu Pro
    370                 375                 380

Glu Ala Gln His Lys Ala Glu Val Tyr Thr Lys Gln Gly Phe Gly Asn
385                 390                 395                 400

Leu Pro Ile Cys Met Ala Lys Thr His Leu Ser Leu Ser His Asn Pro
                405                 410                 415

Glu Gln Lys Gly Val Pro Thr Gly Phe Ile Leu Pro Ile Arg Asp Ile
                420                 425                 430

Arg Ala Ser Val Gly Ala Gly Phe Leu Tyr Pro Leu Val Gly Thr Met
                435                 440                 445

Ser Thr Met Pro Gly Leu Pro Thr Arg Pro Cys Phe Tyr Asp Ile Asp
    450                 455                 460

Leu Asp Pro Glu Thr Glu Gln Val Asn Gly Leu Phe
465                 470                 475

<210> SEQ ID NO 2
<211> LENGTH: 747
<212> TYPE: PRT
<213> ORGANISM: Homo sapiens

<400> SEQUENCE: 2

Met Pro Leu Phe Lys Leu Pro Ala Glu Glu Lys Gln Ile Asp Asp Ala
1               5                   10                  15

Met Arg Asn Phe Ala Glu Lys Val Phe Ala Ser Glu Val Lys Asp Glu
                20                  25                  30

Gly Gly Arg Gln Glu Ile Ser Pro Phe Asp Val Asp Glu Ile Cys Pro
            35                  40                  45

Ile Ser His His Glu Met Gln Ala His Ile Phe His Leu Glu Thr Leu
50                  55                  60

Ser Thr Ser Thr Glu Ala Arg Arg Lys Lys Arg Phe Gln Gly Arg Lys
65                  70                  75                  80

Thr Val Asn Leu Ser Ile Pro Leu Ser Glu Thr Ser Ser Thr Lys Leu
                85                  90                  95

Ser His Ile Asp Glu Tyr Ile Ser Ser Pro Thr Tyr Gln Thr Val
                100                 105                 110

Pro Asp Phe Gln Arg Val Gln Ile Thr Gly Asp Tyr Ala Ser Gly Val
            115                 120                 125

Thr Val Glu Asp Phe Glu Ile Val Cys Lys Gly Leu Tyr Arg Ala Leu
130                 135                 140

Cys Ile Arg Glu Lys Tyr Met Gln Lys Ser Phe Gln Arg Phe Pro Lys
145                 150                 155                 160

Thr Pro Ser Lys Tyr Leu Arg Asn Ile Asp Gly Glu Ala Trp Val Ala
                165                 170                 175

Asn Glu Ser Phe Tyr Pro Val Phe Thr Pro Pro Val Lys Lys Gly Glu
                180                 185                 190

Asp Pro Phe Arg Thr Asp Asn Leu Pro Glu Asn Leu Gly Tyr His Leu
            195                 200                 205

Lys Met Lys Asp Gly Val Val Tyr Val Tyr Pro Asn Glu Ala Ala Val
210                 215                 220

Ser Lys Asp Glu Pro Lys Pro Leu Pro Tyr Pro Asn Leu Asp Thr Phe
225                 230                 235                 240

Leu Asp Asp Met Asn Phe Leu Leu Ala Leu Ile Ala Gln Gly Pro Val
                245                 250                 255

Lys Thr Tyr Thr His Arg Arg Leu Lys Phe Leu Ser Ser Lys Phe Gln
                260                 265                 270
```

-continued

```
Val His Gln Met Leu Asn Glu Met Asp Glu Leu Lys Glu Leu Lys Asn
        275                 280                 285
Asn Pro His Arg Asp Phe Tyr Asn Cys Arg Lys Val Asp Thr His Ile
        290                 295                 300
His Ala Ala Ala Cys Met Asn Gln Lys His Leu Leu Arg Phe Ile Lys
305                 310                 315                 320
Lys Ser Tyr Gln Ile Asp Ala Asp Arg Val Val Tyr Ser Thr Lys Glu
                325                 330                 335
Lys Asn Leu Thr Leu Lys Glu Leu Phe Ala Lys Leu Lys Met His Pro
            340                 345                 350
Tyr Asp Leu Thr Val Asp Ser Leu Asp Val His Ala Gly Arg Gln Thr
        355                 360                 365
Phe Gln Arg Phe Asp Lys Phe Asn Asp Lys Tyr Asn Pro Val Gly Ala
        370                 375                 380
Ser Glu Leu Arg Asp Leu Tyr Leu Lys Thr Asp Asn Tyr Ile Asn Gly
385                 390                 395                 400
Glu Tyr Phe Ala Thr Ile Ile Lys Glu Val Gly Ala Asp Leu Val Glu
                405                 410                 415
Ala Lys Tyr Gln His Ala Glu Pro Arg Leu Ser Ile Tyr Gly Arg Ser
            420                 425                 430
Pro Asp Glu Trp Ser Lys Leu Ser Ser Trp Phe Val Cys Asn Arg Ile
        435                 440                 445
His Cys Pro Asn Met Thr Trp Met Ile Gln Val Pro Arg Ile Tyr Asp
        450                 455                 460
Val Phe Arg Ser Lys Asn Phe Leu Pro His Phe Gly Lys Met Leu Glu
465                 470                 475                 480
Asn Ile Phe Met Pro Val Phe Glu Ala Thr Ile Asn Pro Gln Ala Asp
                485                 490                 495
Pro Glu Leu Ser Val Phe Leu Lys His Ile Thr Gly Phe Asp Ser Val
            500                 505                 510
Asp Asp Glu Ser Lys His Ser Gly His Met Phe Ser Ser Lys Ser Pro
        515                 520                 525
Lys Pro Gln Glu Trp Thr Leu Glu Lys Asn Pro Ser Tyr Thr Tyr Tyr
        530                 535                 540
Ala Tyr Tyr Met Tyr Ala Asn Ile Met Val Leu Asn Ser Leu Arg Lys
545                 550                 555                 560
Glu Arg Gly Met Asn Thr Phe Leu Phe Arg Pro His Cys Gly Glu Ala
                565                 570                 575
Gly Ala Leu Thr His Leu Met Thr Ala Phe Met Ile Ala Asp Asp Ile
            580                 585                 590
Ser His Gly Leu Asn Leu Lys Lys Ser Pro Val Leu Gln Tyr Leu Phe
        595                 600                 605
Phe Leu Ala Gln Ile Pro Ile Ala Met Ser Pro Leu Ser Asn Asn Ser
        610                 615                 620
Leu Phe Leu Glu Tyr Ala Lys Asn Pro Phe Leu Asp Phe Leu Gln Lys
625                 630                 635                 640
Gly Leu Met Ile Ser Leu Ser Thr Asp Pro Met Gln Phe His Phe
                645                 650                 655
Thr Lys Glu Pro Leu Met Glu Glu Tyr Ala Ile Ala Ala Gln Val Phe
            660                 665                 670
Lys Leu Ser Thr Cys Asp Met Cys Glu Val Ala Arg Asn Ser Val Leu
        675                 680                 685
Gln Cys Gly Ile Ser His Glu Glu Lys Val Lys Phe Leu Gly Asp Asn
```

```
                    690                695                700
Tyr Leu Glu Glu Gly Pro Ala Gly Asn Asp Ile Arg Arg Thr Asn Val
705                     710                715                720

Ala Gln Ile Arg Met Ala Tyr Arg Tyr Glu Thr Trp Cys Tyr Glu Leu
                    725                730                735

Asn Leu Ile Ala Glu Gly Leu Lys Ser Thr Glu
                    740                745

<210> SEQ ID NO 3
<211> LENGTH: 592
<212> TYPE: PRT
<213> ORGANISM: Homo sapiens

<400> SEQUENCE: 3

Met Ala Pro Gly Gln Leu Ala Leu Phe Ser Val Ser Asp Lys Thr Gly
1                   5                   10                  15

Leu Val Glu Phe Ala Arg Asn Leu Thr Ala Leu Gly Leu Asn Leu Val
                    20                  25                  30

Ala Ser Gly Gly Thr Ala Lys Ala Leu Arg Asp Ala Gly Leu Ala Val
                    35                  40                  45

Arg Asp Val Ser Glu Leu Thr Gly Phe Pro Glu Met Leu Gly Gly Arg
50                  55                  60

Val Lys Thr Leu His Pro Ala Val His Ala Gly Ile Leu Ala Arg Asn
65                  70                  75                  80

Ile Pro Glu Asp Asn Ala Asp Met Ala Arg Leu Asp Phe Asn Leu Ile
                    85                  90                  95

Arg Val Val Ala Cys Asn Leu Tyr Pro Phe Val Lys Thr Val Ala Ser
                    100                 105                 110

Pro Gly Val Thr Val Glu Glu Ala Val Glu Gln Ile Asp Ile Gly Gly
                    115                 120                 125

Val Thr Leu Leu Arg Ala Ala Ala Lys Asn His Ala Arg Val Thr Val
                    130                 135                 140

Val Cys Glu Pro Glu Asp Tyr Val Val Val Ser Thr Glu Met Gln Ser
145                 150                 155                 160

Ser Glu Ser Lys Asp Thr Ser Leu Glu Thr Arg Arg Gln Leu Ala Leu
                    165                 170                 175

Lys Ala Phe Thr His Thr Ala Gln Tyr Asp Glu Ala Ile Ser Asp Tyr
                    180                 185                 190

Phe Arg Lys Gln Tyr Ser Lys Gly Val Ser Gln Met Pro Leu Arg Tyr
                    195                 200                 205

Gly Met Asn Pro His Gln Thr Pro Ala Gln Leu Tyr Thr Leu Gln Pro
                    210                 215                 220

Lys Leu Pro Ile Thr Val Leu Asn Gly Ala Pro Gly Phe Ile Asn Leu
225                 230                 235                 240

Cys Asp Ala Leu Asn Ala Trp Gln Leu Val Lys Glu Leu Lys Glu Ala
                    245                 250                 255

Leu Gly Ile Pro Ala Ala Ala Ser Phe Lys His Val Ser Pro Ala Gly
                    260                 265                 270

Ala Ala Val Gly Ile Pro Leu Ser Glu Asp Glu Ala Lys Val Cys Met
                    275                 280                 285

Val Tyr Asp Leu Tyr Lys Thr Leu Thr Pro Ile Ser Ala Ala Tyr Ala
                    290                 295                 300

Arg Ala Arg Gly Ala Asp Arg Met Ser Ser Phe Gly Asp Phe Val Ala
305                 310                 315                 320

Leu Ser Asp Val Cys Asp Val Pro Thr Ala Lys Ile Ile Ser Arg Glu
```

```
                     325                 330                 335
Val Ser Asp Gly Ile Ile Ala Pro Gly Tyr Glu Glu Ala Leu Thr
            340                 345                 350

Ile Leu Ser Lys Lys Lys Asn Gly Asn Tyr Cys Val Leu Gln Met Asp
            355                 360                 365

Gln Ser Tyr Lys Pro Asp Glu Asn Glu Val Arg Thr Leu Phe Gly Leu
    370                 375                 380

His Leu Ser Gln Lys Arg Asn Asn Gly Val Val Asp Lys Ser Leu Phe
385                 390                 395                 400

Ser Asn Val Val Thr Lys Asn Lys Asp Leu Pro Glu Ser Ala Leu Arg
                405                 410                 415

Asp Leu Ile Val Ala Thr Ile Ala Val Lys Tyr Thr Gln Ser Asn Ser
            420                 425                 430

Val Cys Tyr Ala Lys Asn Gly Gln Val Ile Gly Ile Gly Ala Gly Gln
        435                 440                 445

Gln Ser Arg Ile His Cys Thr Arg Leu Ala Gly Asp Lys Ala Asn Tyr
    450                 455                 460

Trp Trp Leu Arg His His Pro Gln Val Leu Ser Met Lys Phe Lys Thr
465                 470                 475                 480

Gly Val Lys Arg Ala Glu Ile Ser Asn Ala Ile Asp Gln Tyr Val Thr
                485                 490                 495

Gly Thr Ile Gly Glu Asp Glu Asp Leu Ile Lys Trp Lys Ala Leu Phe
            500                 505                 510

Glu Glu Val Pro Glu Leu Leu Thr Glu Ala Glu Lys Lys Glu Trp Val
        515                 520                 525

Glu Lys Leu Thr Glu Val Ser Ile Ser Ser Asp Ala Phe Phe Pro Phe
    530                 535                 540

Arg Asp Asn Val Asp Arg Ala Lys Arg Ser Gly Val Ala Tyr Ile Ala
545                 550                 555                 560

Ala Pro Ser Gly Ser Ala Ala Asp Lys Val Val Ile Glu Ala Cys Asp
                565                 570                 575

Glu Leu Gly Ile Ile Leu Ala His Thr Asn Leu Arg Leu Phe His His
            580                 585                 590

<210> SEQ ID NO 4
<211> LENGTH: 194
<212> TYPE: PRT
<213> ORGANISM: Homo sapiens

<400> SEQUENCE: 4

Met Ala Ala Ser Leu Val Gly Lys Lys Ile Val Phe Val Thr Gly Asn
1               5                   10                  15

Ala Lys Lys Leu Glu Glu Val Val Gln Ile Leu Gly Asp Lys Phe Pro
            20                  25                  30

Cys Thr Leu Val Ala Gln Lys Ile Asp Leu Pro Glu Tyr Gln Gly Glu
        35                  40                  45

Pro Asp Glu Ile Ser Ile Gln Lys Cys Gln Glu Ala Val Arg Gln Val
    50                  55                  60

Gln Gly Pro Val Leu Val Glu Asp Thr Cys Leu Cys Phe Asn Ala Leu
65                  70                  75                  80

Gly Gly Leu Pro Gly Pro Tyr Ile Lys Trp Phe Leu Glu Lys Leu Lys
                85                  90                  95

Pro Glu Gly Leu His Gln Leu Leu Ala Gly Phe Glu Asp Lys Ser Ala
            100                 105                 110

Tyr Ala Leu Cys Thr Phe Ala Leu Ser Thr Gly Asp Pro Ser Gln Pro
```

```
            115                 120                 125
Val Arg Leu Phe Arg Gly Arg Thr Ser Gly Arg Ile Val Ala Pro Arg
            130                 135                 140

Gly Cys Gln Asp Phe Gly Trp Asp Pro Cys Phe Gln Pro Asp Gly Tyr
145                     150                 155                 160

Glu Gln Thr Tyr Ala Glu Met Pro Lys Ala Glu Lys Asn Ala Val Ser
                165                 170                 175

His Arg Phe Arg Ala Leu Leu Glu Leu Gln Glu Tyr Phe Gly Ser Leu
                180                 185                 190

Ala Ala
```